United States Patent [19]
Leung et al.

[11] Patent Number: 5,567,590
[45] Date of Patent: Oct. 22, 1996

[54] METHODS OF DIAGNOSING STEROID-RESISTANT INFLAMMATION DUE TO TYPE I OR TYPE II NUCLEAR GLUCOCORTICOID RECEPTOR BINDING ABNORMALITIES

[75] Inventors: Donald Y. M. Leung, Englewood; Stanley J. Szefler, Aurora; Joseph D. Spahn, Denver, all of Colo.

[73] Assignee: National Jewish Center for Immunology and Respiratory, Denver, Colo.

[21] Appl. No.: 178,220

[22] Filed: Jan. 6, 1994

[51] Int. Cl.$^6$ .......................... C07K 14/72; G01N 33/53; G01N 33/567

[52] U.S. Cl. .......................... 435/7.2; 435/7.1; 435/7.21; 436/501; 436/503; 436/504; 514/825; 514/826; 514/886

[58] Field of Search ......................... 435/7.1, 7.2, 7.21; 436/501, 503, 504; 514/826, 825, 886

[56] References Cited

PUBLICATIONS

Peterson et al. 1981. J. Allergy Clin. Immunol. 68: 212–217.
Sher et al. 1992. J. Allergy Clin. Immunol. 89:285.
Muller et al. 1991. Biochim. et Biophys. Acta 1088: 171–182.
Kam et al., "Combination IL-2 and IL-4 Reduces Glucocorticoid Receptor-Binding Affinity and T Cell Response to Glucocorticoids", pp. 3460–3466, 1993, J. Immunol., vol. 151, Oct.

*Primary Examiner*—Stephen G. Walsh
*Assistant Examiner*—Elizabeth C. Kemmerer
*Attorney, Agent, or Firm*—Sheridan Ross & McIntosh

[57] ABSTRACT

Disclosed is a method for diagnosing inflammation in an animal which includes analyzing cells to assess glucocorticoid receptor binding affinity or glucocorticoid receptor number. A low binding affinity and high receptor number are each indicative of inflammation. Also disclosed is a method for treating inflammation in an animal, which inflammation causes glucocorticoid receptor alteration which includes suppressing the activity or expression of cytokines which, in the absence of suppression, alter glucocorticoid receptors. Also disclosed are methods for identifying Type II glucocorticoid receptor binding abnormality and for distinguishing Type I glucocorticoid receptor binding abnormalities from Type II. Further disclosed are treatments for steroid-resistant inflammatory disorders induced by IL-2 and IL-4 which are associated with glucocorticoid receptor binding abnormalities. The treatment includes administering an agent which is an IL-2 suppressor and/or an IL-4 suppressor.

6 Claims, 13 Drawing Sheets

Journal of Immunology

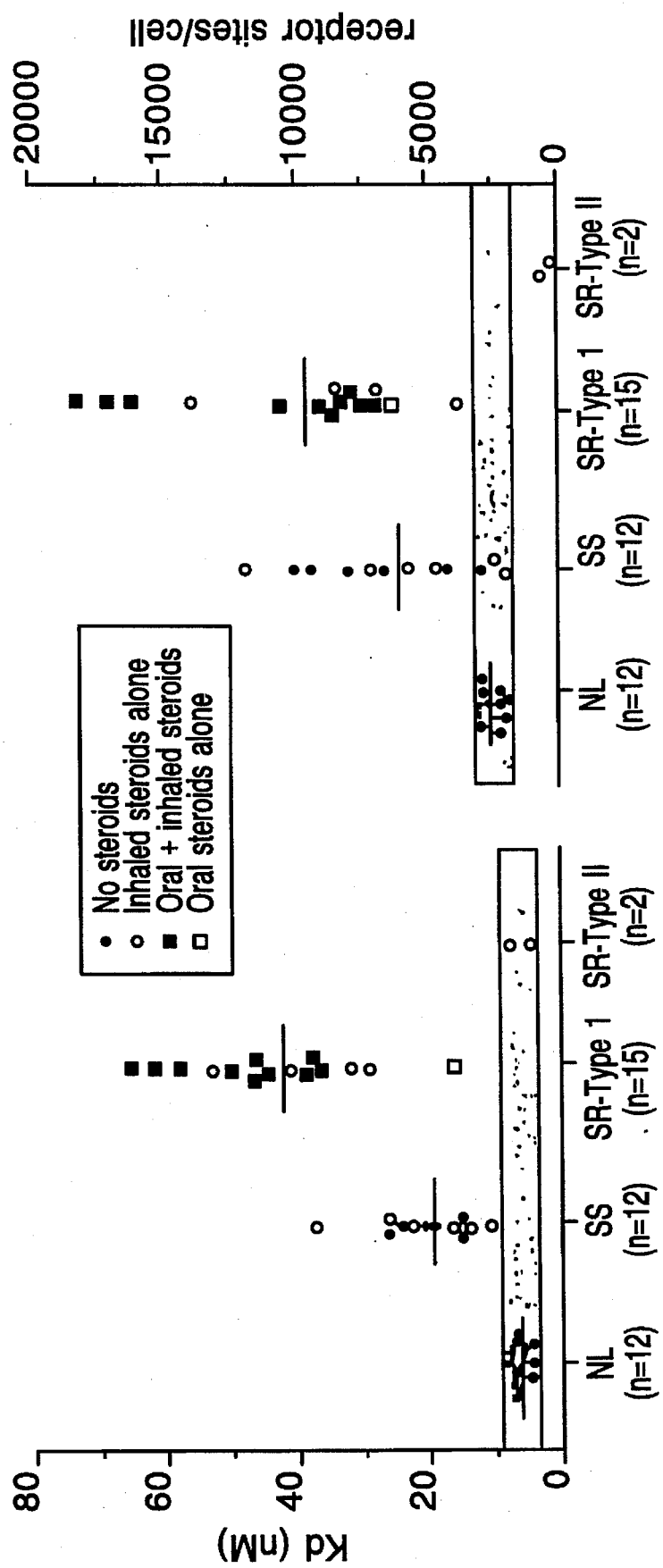

METHODS OF DIAGNOSING STEROID-RESISTANT INFLAMMATION DUE TO TYPE I OR TYPE II NUCLEAR GLUCOCORTICOID RECEPTOR BINDING ABNORMALITIES

This invention was made with government support under USPHS Grant HL36577 awarded by the National Institutes of Health. The government has certain rights to this invention.

FIELD OF THE INVENTION

The present invention pertains to methods for diagnosing and treating inflammatory disorders, particularly inflammatory disorders which are steroid resistant and/or which involve glucocorticoid abnormalities.

SUMMARY OF THE INVENTION

The present invention is directed to a method for diagnosing and treating inflammation in an animal, comprising analyzing cells from an animal to assess the glucocorticoid receptor binding affinity or glucocorticoid receptor number wherein a low binding affinity and high receptor number, individually or collectively, are indicative of inflammation. A method is disclosed whereby allergic inflammation and potential response to steroid therapy is assessed and monitored by alterations in glucocorticoid receptor binding parameters. The present invention also relates to a method for monitoring inflammation in an animal, diagnosing the extent of inflammation in an animal, predicting therapies to counteract glucocorticoid receptor binding abnormalities and to formulate successful therapies for treating inflammation, particularly in glucocorticoid resistant animals. The level of allergic inflammation directly corresponds to glucocorticoid receptor abnormalities and as such, such abnormalities are a marker of the extent of inflammation. In response to inflammation, cytokine production is triggered which alters glucocorticoid receptors, making cells resistant to glucocorticoids. It is believed that particular cytokines, such as IL-2 and IL-4, induce the production of transcription factors such as AP1, NF-Kappa B, etc., capable of binding to glucocorticoid receptors, thereby reducing receptor activity.

One aspect of the present invention relates to a method for diagnosing inflammation in an animal where the culturing of cells, in vitro and in the absence of IL-2 and IL-4, restores normal glucocorticoid receptor binding affinity and glucocorticoid receptor numbers. The method further includes determining whether cells cultured in vitro in the presence of IL-2 and IL-4 maintain low glucocorticoid receptor binding affinity and high numbers of glucocorticoid receptors. The present method can be used to diagnose allergic inflammatory disorders and rheumalogical inflammatory disorders including, but not limited to chronic allergic inflammation, asthma, atopic dermatitis, allergic rhinitis, rheumatoid arthritis and systemic lupus.

Another aspect of the present invention relates to a method for treating inflammation that causes glucocorticoid receptor alteration in an animal comprising suppressing the activity or expression of cytokines which, in the absence of cytokine suppression, alter glucocorticoid receptors. In one embodiment, the cytokines suppressed comprise IL-2 and IL-4 and such suppression can be accomplished by administering an steroid-independent immune suppressive drug including, but not limited to cyclosporin, troleandomycin, methotrexate, gold, intravenous gamma globulin and mixtures thereof.

The present invention is particularly directed to a method for diagnosing and treating two separate types of glucocorticoid receptor abnormalities, denoted as Type I and Type II. A method for identifying animals having Type II glucocorticoid receptor binding abnormalities is described wherein glucocorticoid receptor numbers in glucocorticoid receptor-producing cells recovered from animals is determined and those animals having an abnormally low number of glucocorticoid receptors are identified as having the Type II abnormality. A method for distinguishing Type I and Type II glucocorticoid receptor binding abnormalities entails the determination of glucocorticoid receptor numbers or glucocorticoid binding affinities in glucocorticoid receptor producing cells isolated from an animal, identifying cells as Type I that have low glucocorticoid receptor binding affinities or high glucocorticoid receptor numbers, and identifying cells as Type II that have low glucocorticoid receptor numbers or normal glucocorticoid receptor binding affinities.

The present invention also encompasses a method for prescribing treatment for inflammatory disorders comprising measuring glucocorticoid receptor binding affinity or glucocorticoid receptor number to determine whether a Type I or Type II glucocorticoid receptor binding abnormality exists, and prescribing, in the case of Type I abnormality, a treatment selected from the group consisting of suppressing the activity or expression of cytokines and administering a high dose of glucocorticoids effective to reduce inflammation. In the case of Type II abnormalities, the activity or expression of cytokines is suppressed.

The present invention is also directed to apparatus and kits useful for conducting the various methods of the present invention. Such apparatus and kits include means for determining the glucocorticoid receptor binding affinity and glucocorticoid receptor number of cells. Such means, for example, are disclosed in the description below. Also included are means for suppressing expression of cytokines and/or administering high doses of glucocorticoids, which means are also described below.

BRIEF DESCRIPTION OF THE DRAWINGS

FIGS. 10A and B illustrates the glucocorticoid receptor binding parameters of 12 normal patients, 17 steroid-resistant patients and 12 steroid-sensitive patients.

DETAILED DESCRIPTION OF THE INVENTION

Figure 1:
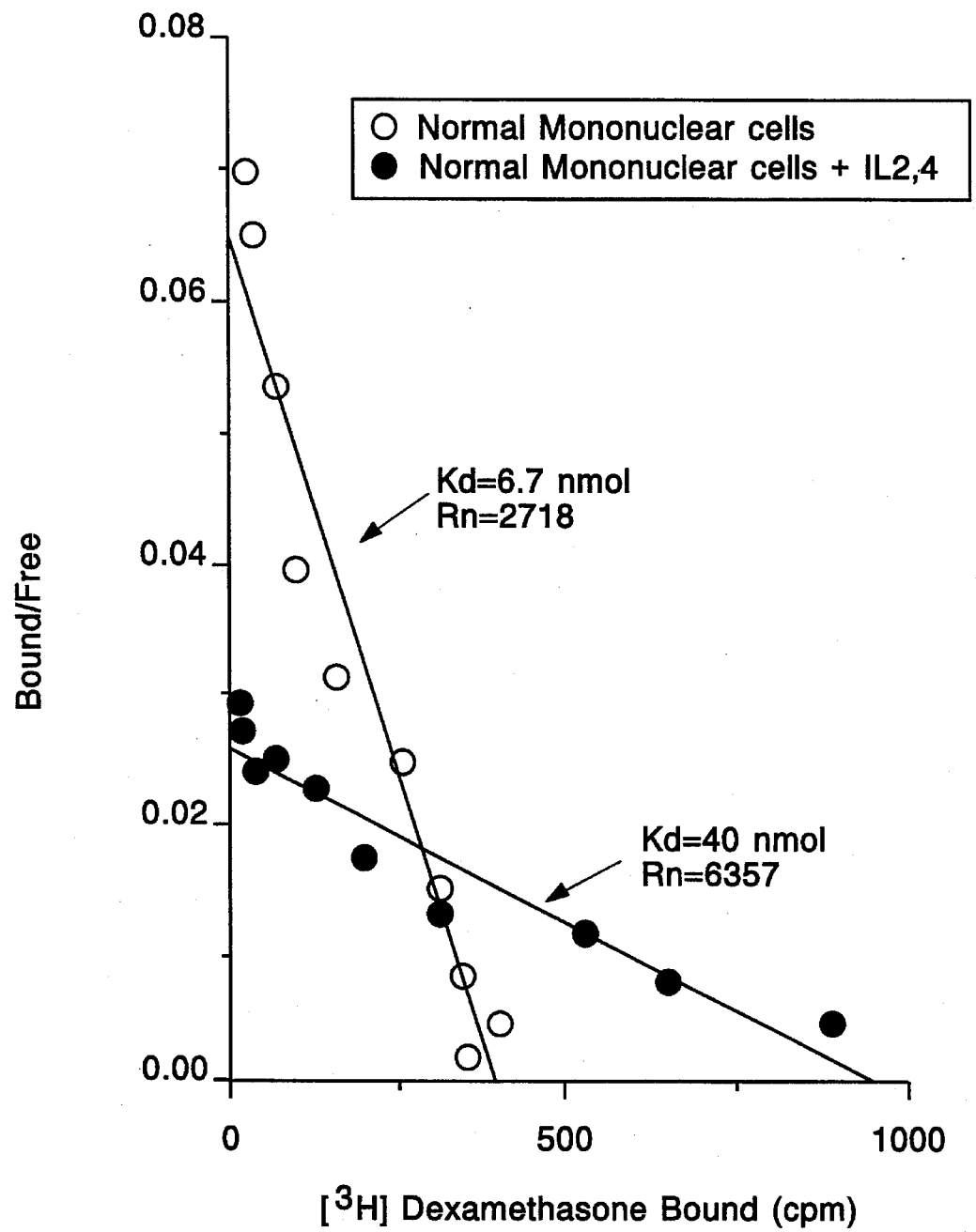
FIG. 1 illustrates a scatchard plot analysis of [$^3$H]dexamethasone radioligand binding data of PBMC from a normal donor treated or not treated with IL-2 and IL-4.

As used herein, the term "diagnosis" refers to the method of distinguishing one disease from another disease and/or determining the nature of a disease.

As used herein, the term "disease" refers to a biological process having a characteristic series of symptoms which result in physical abnormalities.

As used herein, the terms "disorder" or "condition" refer to abnormal biological function. Overcoming GR abnormalities can be accomplished by adding a sufficient amount of glucocorticoids to cells having GR abnormalities to achieve binding of glucocorticoids to existing GR's. Overcoming GR abnormalities can result in decreased levels of cytokines in those animals having GR abnormalities. Overcoming GR abnormalities can also result in decreased inflammation in animals having GR abnormalities.

As used herein, the term "steroid resistant" refers to patients having inflammatory diseases in which administration of steroid treatment, typically effective in patients having such diseases, is ineffective. For example, in the case of asthma patients, steroid resistant patients refers to patients which fail to have an increase of greater than about 15% forced expiratory volume in one second after a one week course of oral prednisone 20 mg twice daily. The term "steroid sensitive" refers to patients of allergic diseases which are not steroid resistant. The term "poorly controlled" refers to patients of allergic diseases who, when treated with at least about 20 mg po bid of prednisone, show GR binding abnormality reversal.

The term "IL-2 suppressor" refers to any agent which suppresses expression of IL-2 and/or activity of IL-2.

The term "IL-4 suppressor" refers to any agent which suppresses expression of IL-2 and/or activity of IL-2.

The term "glucocorticoid (GR) binding abnormality" refers to a condition of an animal in which the glucocorticoid receptor number is abnormally high or abnormally low and/or in which the glucocorticoid receptor binding affinity is abnormally high or abnormally low. It should be noted that the term "animal" refers to any animal, including without limitation avians and mammals and most preferably includes humans. An abnormally low glucocorticoid binding affinity can refer to a binding affinity for nuclear binding sites which is a Kd of greater than about 25 nM, more preferably greater than about 35 nM and more preferably greater than about 50 nM. An abnormally high glucocorticoid receptor number can refer to a nuclear glucocorticoid receptor number of greater than about 6,500 sites per cell, more preferably greater than about 7,000 sites per cell and most preferably greater than about 7,500 sites per cell. Abnormally low glucocorticoid receptor numbers can refer to nuclear glucocorticoid receptor numbers of less than about 2,500 sites per cell, more preferably less than about 7,000 sites per cell and most preferably less than about 1,500 sites per cell.

It should be noted that there are two identified types of glucocorticoid receptor binding abnormalities. The first is herein referred to as "Type I". Type I glucocorticoid receptor binding abnormality refers to a condition in which low binding affinity is present and high glucocorticoid receptor numbers are present. A second type of glucocorticoid receptor binding abnormality is herein referred to "Type II". Type II refers to as a condition in which low glucocorticoid receptor numbers are present. It should be noted that glucocorticoid receptor binding abnormalities can be either reversible or non-reversible. For example, Type I glucocorticoid receptor binding abnormality has been found to be reversible when cells are grown in vitro in the absence of both IL-2 and IL-4. In contrast, Type II glucocorticoid receptor binding abnormality is non-reversible.

As used herein, the term "high dose of glucocorticoid" means an amount significantly greater than that normally prescribed for anti-inflammatory effects. Such amounts are typically twice, preferably three times, and more preferably four times the normal prescribed amounts.

As used herein, the term "steroid resistant inflammatory disorders" refers to abnormal physical states resulting from inflammation of tissue, and cells involved in the inflammation are steroid resistant.

Methods of the present invention are suitable for use in conjunction with inflammation associated with a variety of disorders, including without limitation, allergic inflammatory disorders, such as allergic inflammation, asthma, atopic dermatitis and allergic rhinitis, and rheumalogical disorders such as rheumatoid arthritis and systemic lupus. For purposes of illustration only, the following discussion will focus on asthma.

Airway inflammation and immune activation play a significant role in the pathogenesis of asthma. Activation of T lymphocytes and eosinophils contributes to the generation and maintenance of the pathogenesis of asthma. T lymphocytes and eosinophils infiltrate into the bronchial mucosa of asthmatics. Evidence for T cell activation in asthma is indicated by elevated levels of soluble IL-2 receptor (sIL-2R) in both serum and bronchoalveolar lavage fluid (BAL) from patients with symptomatic asthma. In addition, BAL cells from atopic asthmatics have shown increased levels of mRNA for IL-2, IL-4, and IL-5, cytokines primarily produced by T lymphocytes. This cytokine profile can be characteristic of cytokine profiles produced by the $T_h2$ T lymphocyte. The $T_h2$ subset can be involved in the pathogenesis of allergic inflammation in that the cytokines it produces are essential for IgE production (IL-4), and the differentiation, proliferation, accumulation, and activation of eosinophils (IL-5). IL-2 acts in an autocrine fashion to stimulate T lymphocyte proliferation and activation. Concomitant to the production of IL-2, is the up regulation of its receptor (CD25).

The eosinophil is as a major effector cell involved in allergic inflammation. By virtue of its ability to produce several lipid-derived proinflammatory mediators such as leukotriene $C_4$ ($LTC_4$), platelet activating factor (PAF), and to secrete pre-formed granule proteins, such as major basic protein (MBP) and ECP, the eosinophil can mediate much of the allergic inflammatory response. The eosinophil granule proteins are cytotoxic, damaging respiratory epithelial cells in vitro, and induce bronchial hyper-responsiveness after in vivo instillation in a primate model.

Glucocorticoids are highly profiled as first line therapy for asthma to reduce airway inflammation and immune activation. Inhaled glucocorticoids are particularly effective for early intervention. Certain subsets of asthmatic patients fail to improve their pulmonary function despite systemic and inhaled glucocorticoid therapy. After careful clinical assessment for poor response, such as other pulmonary abnormalities, poor technique or adherence to medication schedules, pharmacokinetic abnormalities in medication absorption, distribution, or elimination, and concomitant medical or psychological disorders, questions may be raised whether persistent airway inflammation itself or genetic abnormalities in GR binding contributes to poor glucocorticoid response. Certain asthma patients fail to respond to combined systemic and inhaled glucocorticoid treatment despite very high doses over extended treatment periods. Many of these patients continue treatment with glucocorticoids despite the onset of serious adverse effects and poor clinical response. These patients require alternative approaches to treatment. It is therefore important to understand the mechanisms underlying this apparent steroid resistance.

In these steroid resistant (SR) asthmatics, glucocorticoids fail to inhibit T cell proliferation and reduce cytokine secretion. Following a course of systemic glucocorticoids, the percentage of activated T cells in peripheral blood and especially BAL fluid remain elevated in SR but not SS asthmatics. Furthermore, increased levels of IL-2 and IL-4 expressing T cells are present in the bronchoalveolar (BAL) of patients with SR asthma. T cells from peripheral blood of SR asthmatics, but not steroid-sensitive (SS) asthmatics, are persistently activated despite continued treatment with aggressive steroid therapy. Glucocorticoids bind to a specific intracellular receptor to inhibit activation of T cells by various stimuli.

Mechanisms for steroid resistance in asthma are poorly defined. Chronic asthma is associated with a spectrum of glucocorticoid receptor (GR) binding abnormalities with the poorest binding affinity associated with those asthmatics poorly controlled on oral GC therapy. However, even moderate asthmatics had decreased GR binding affinity. A potentially important consequence of on-going airway inflammation and immune activation (apart from the direct effects on the airway epithelium) involves the acquisition of diminished GR binding affinity as, for example in PBMC's from SR asthmatics. While not being bound by theory, one possibility is that T cells remain persistently activated in SR asthma because of an alteration in glucocorticoid receptor (GR) binding. T cells obtained from SR asthmatics have a substantially lower binding affinity for glucocorticoids and higher GR number than normals (non-asthmatics) or steroid sensitive (SS) asthmatics. Cyclosporin A, but not glucocorticoids, inhibit PHA-driven T cell proliferation and cytokine secretion in SR asthmatics. Similar to patients responding to identical glucocorticoid doses, most SR asthmatics develop cushingoid features and a reduced morning plasma cortisol concentration. Thus, steroid resistance and/or sensitivity could be due to local cytokine secretion.

Experiment 1—Effects of IL-2 and IL-4 on PBMC and T cell GR binding.

Reagents

Phorbol myristate acetate (PMA) was obtained from Sigma Chemical Co. (St. Louis, Mo.). 'I' was obtained from Calbiochem (La Jolla, Calif.). IL-2 was obtained from the Cetus Corp. (Emeryville, Calif.) and IL-4 was obtained from Schering-Plough Research (Bloomfield, N.J.). IFN-γ was obtained from Genentech (South San Francisco, Calif.).

Cell Isolation

Peripheral blood was collected in a heparinized syringe from seven normal donors with no history of atopy and from four SR asthmatics. Asthmatics were defined as SR if they failed to improve their morning pre-bronchodilator forced expiratory volume in 1 second ($FEV_1$) by ≧15% after a 1 week course of prednisone at a minimum oral dose of 40 mg/day. Peripheral blood mononuclear cells (PBMC) were obtained by Ficoll-Paque (Pharmacia, Piscataway, N.J.) gradient centrifugation. T cells were isolated by sheep E rosetting (Colorado Serum Co., Denver, Colo.), and the (E−) non-T cell population was further purified by lysis with anti-CD3 antibody (Ortho Diagnostic Systems, Raritan, N.J.) and rabbit complement c (GIBCO, Grand Island, N.Y.). This procedure yielded an E(+) fraction of >97% T cell purity and <1% B cells. The E(−) fraction contained <5% T cells.

Cell Culture and Proliferation Studies

Normal SS and SR PBMC were isolated and resuspended at a concentration of $1\times10^6$ cells/ml in RPMI 1640 (Bioproducts, Walkersville, Md.) containing 10% heat-inactivated fetal calf serum (FCS) (HyClone Labs., Logan, Utah), L-glutamine (4 mmol), penicillin (100 U/ml), streptomycin (100 μg/ml), and HEPES (20 mM solution) in the presence and absence of IL-2 (50 U/ml) and/or IL-4 (50 U/ml) for 48 hours at 37° C. in 5% $CO_2$.

PBMC were then analyzed for GR-binding parameters or capacity to proliferate in the absence and presence of methylprednisone (MPN). For proliferation studies, PBMC ($2\times10^5$ cells/200 ml) were plated in triplicate in 96-well, flat bottom culture plates (Nunclon, Denmark) using the original culture medium with PMA (0.01 μM), ionomycin (0.05 μM), and varying MPN concentrations ($10^{-6}$ to $10^{-9}$M). After 72 hours of incubation, proliferation was measured by [$^3$H]TdR incorporation (1 μCi/well, 6.7 Ci/mmol; ICN, Irvine, Calif.) during the last 6 hours of culture. Proliferation response was measured as the percent of control incorporation of [$^3$]TdR using the formula:

$$\% \text{ of Control response} = 1 - \frac{(MPN + PMA/I)}{PMA/I \text{ control}} \times 100.$$

GR-Binding Studies

A [$^3$H]dexamethasone radioligand-binding assay and Scatchard analysis, as previously described (Crabtree et al., p. 252, 1981, in Methods of Hematology: The Leukemic Cell, Catovsky, Chanarin, Beutler, Brown and Jacobs, eds., New York), was used to obtain nuclear and cytosolic GR-binding parameters in PBMC from normal and SR asthmatic donors. Radioligand-binding studies were performed with [$^3$H]dexamethasone (specific activity=37 to 39 Ci/mmol) purchased from Amersham International (Arlington Heights, Ill.). After purification, the cells were centrifuged and resuspended in RPMI 1640 buffer solution to a minimum of $75\times10^6$ cells/ml and stored on ice. The cells were then distributed into 1.5 ml microcentrifuge tubes to obtain $1.5\times10^6$ cells/tube. Cells were then incubated in RPMI 1640 buffer solution with 10 different concentrations of [$^3$H] dexamethasone ranging from 0.8 to 400 nM in duplicate in the presence and absence of 1000-fold excess of unlabeled dexamethasone. The cells were incubated with labeled dexamethasone at 37° C. for 1 hour in a shaking water bath. For measurement of nonspecific binding, a single measurement obtained in duplicate was derived from a solution of 20 nM [$^3$H]dexamethasone and 2 μM of unlabeled dexamethasone (Sigma) was used for the nuclear and cytosolic components.

After incubation, all tubes were centrifuged at 12,000×g for 2 minutes and 20 μl of supernatant were removed and placed in a counting vial with 5 ml liquid scintillation cocktail (Biosafe 11, Research Products International Corp., Mt. Prospect, Ill.) and counted in a Beckman Scintillation Counter to measure the free [$^3$H]dexamethasone concentration. The tubes were then cooled to 3° C. in an ice bath. Measurements of glucocorticoid bound to nuclear receptors were obtained by hypotonic lysis of one set of PBMC. PBMC were incubated with 1.2 ml of 1.5 mM MgCl$_2$ with 10 mM Na$_2$MoO$_4$ solution, mixed, and left at 3° C. in an ice bath for 30 minutes to complete lysis. The tubes were then centrifuged at 12,000×g for 5 minutes and the supernatant was carefully aspirated, with the nuclear fraction left undisturbed. The tube was then inverted and drained for 15 minutes. The microcentrifuge tube tip was then cut and placed in 5 ml liquid scintillation cocktail for counting.

Cytosolic receptors were obtained after hypotonic lysis of a separate set of PBMC with 100 μl of 1.5 mM MgCl$_2$ containing dextran-coated charcoal (10 ml of 1.5 mM MgCl$_2$ plus 0.1 g of charcoal and 0.01 g dextran Molecular Weight (MW) 60,000 to 90,000), mixed vigorously, and left in an ice bath at 3° C. for 30 minutes to complete lysis. The cells were then centrifuged at 12,000×g for 5 minutes and 100 μl of supernatant removed for counting. Analysis of the two resulting fractions assumed that GR binding is saturable whereas nonspecific binding is nonsaturable.

All values obtained for both cytoplasmic and nuclear-bound glucocorticoid were corrected for nonsaturable binding for each respective concentration. Saturation binding analysis was performed assuming a linear binding plot of the bound divided by the free [$^3$H]dexamethasone concentration versus the amount bound, and extrapolating to the amount bound at an infinite free hormone concentration. A least squares linear regression fit was used to define the binding parameters, specifically, receptor sites per cell and binding affinity.

Effect of cytokines on GR-binding affinity and number

Figures 2A, 2B:
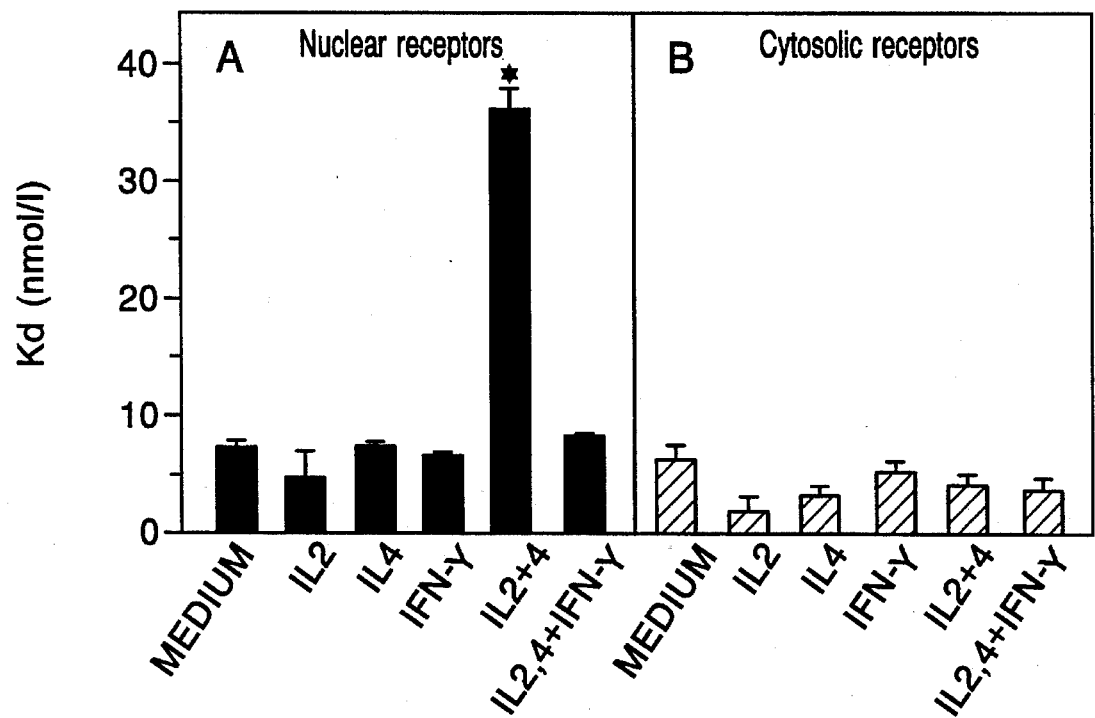
FIGS. 2A–D illustrates the effect of either IL-2 or IL-4 on nuclear glucocorticoid receptor binding.
Figures 2C, 2D:
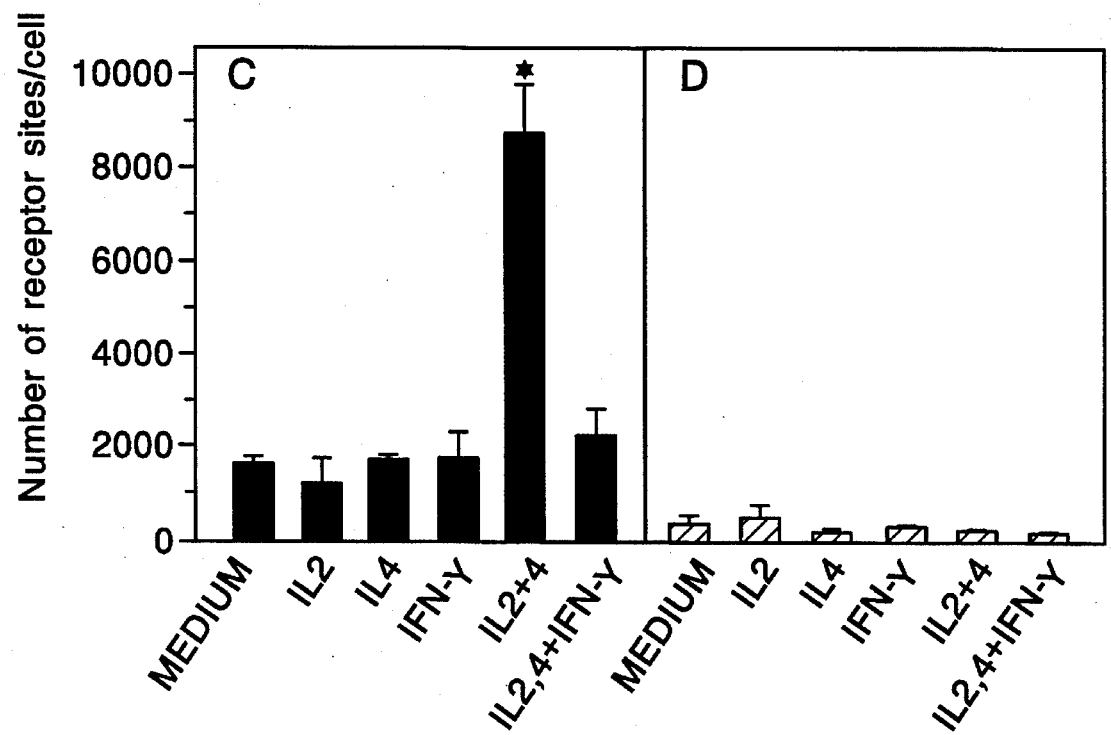

FIG. 1 shows the Scatchard plot of [$^3$H]dexamethasone radioligand-binding data of PBMC from a normal donor in medium alone and also preincubated with the combination of IL-2 (50 U/ml)+IL-4 (50 U/ml) for 48 hours. The cumulative radioligand-binding data from seven normal donors preincubated with IL-2 and IL-4 shows a significant increase (p=0.0001, analysis of variance (ANOVA)) in the $K_d$, i.e., a decrease in binding affinity for glucocorticoids (FIG. 2A, each bar represents the mean±SEM), and an increased GR number in the nuclear fraction of the PBMC when compared with medium alone (FIG. 2C). In contrast, preincubation with either IL-2 or IL-4 individually had no effect on nuclear GR $K_d$. Cytokines had no significant effect on cytosolic GR $K_d$ and receptor number (FIGS. 2, B and D). Furthermore, these observations were not related to a change in total cell number after preincubation of PBMC with IL-2+IL-4 for 48 hours.

In addition, the GR-binding parameters of PBMC were studied by incubating the PBMC's with IL-2+IL-4 for up to 96 hours. As shown in Table 1, the maximal effect on GR $K_d$ was reached after 48 hours of incubation and did not increase further with a longer duration of incubation.

TABLE 1

Time course of GR $K_d$ response to IL-2 + IL-4

| Normal Controls | $K_d$ (nM) | | | | |
|---|---|---|---|---|---|
| | 0 h | 24 h | 48 h | 72 h | 96 h |
| Subject 1 | 5.9 | 6.4 | 36 | 33 | 32 |
| Subject 2 | 6.3 | 9.6 | 42 | ND$^a$ | 31 |
| Subject 3 | 6.6 | 7.0 | 40 | 36 | 36 |

$^a$ND, not determined

Of note, this effect of IL-2+IL-4 on GR binding was a reversible effect because cells incubated initially for 48 hours with these cytokines showed a decrease in their GR $K_d$ and GR numbers when they were washed and cultured with medium, in the absence of cytokines, for an additional 48 hours (see Table 2).

TABLE 2

Reversibility of GR-binding parameters after incubation with IL-2 + IL-4

| Normal Controls | $K_d$ (nM) | | | Receptor Sites/Cell | | |
|---|---|---|---|---|---|---|
| | 0 h | 48 h | 96 h | 0 h | 48 h | 96 h |
| Subject 1 | | | | | | |
| PBMC | 9.2 | 9.6 | | 3123 | 1592 | |
| PBMC + IL-2 and IL-4 | | 31 | 32 | | 4154 | 9692 |
| PBMC + IL-2 and IL-4 wash$^a$ | | | 18 | | | 1869 |
| Subject 2 | | | | | | |
| PBMC | 6.3 | 5.1 | | 2219 | 1422 | |
| PBMC + IL-2 and IL-4 | | 42 | 43 | | 7539 | 8653 |
| PBMC + IL-2 and IL-4 wash$^a$ | | | 12 | | | 2004 |

$^a$Cytokines were washed out after 48 hours and incubation continued in media alone for another 48 h.

When PBMC from normal donors were preincubated with the combination of IFN-γ (200 U/ml), IL-2 (50 U/ml), and IL-4 (50 U/ml), there was no change in nuclear or cytosolic GR $K_d$ and receptor number (FIGS. 2,A to D) when compared with medium alone. PBMC preincubated with IFN-γ alone resulted in no observed changes in nuclear and cytosolic GR binding. Thus, the changes in nuclear GR $K_d$ and receptor number induced by combination IL-2+IL-4 are inhibited by co-incubation with IFN-γ.

Functional effects of IL-2+IL-4 on PBMC response to methylprednisone (MPN)

Figure 3:
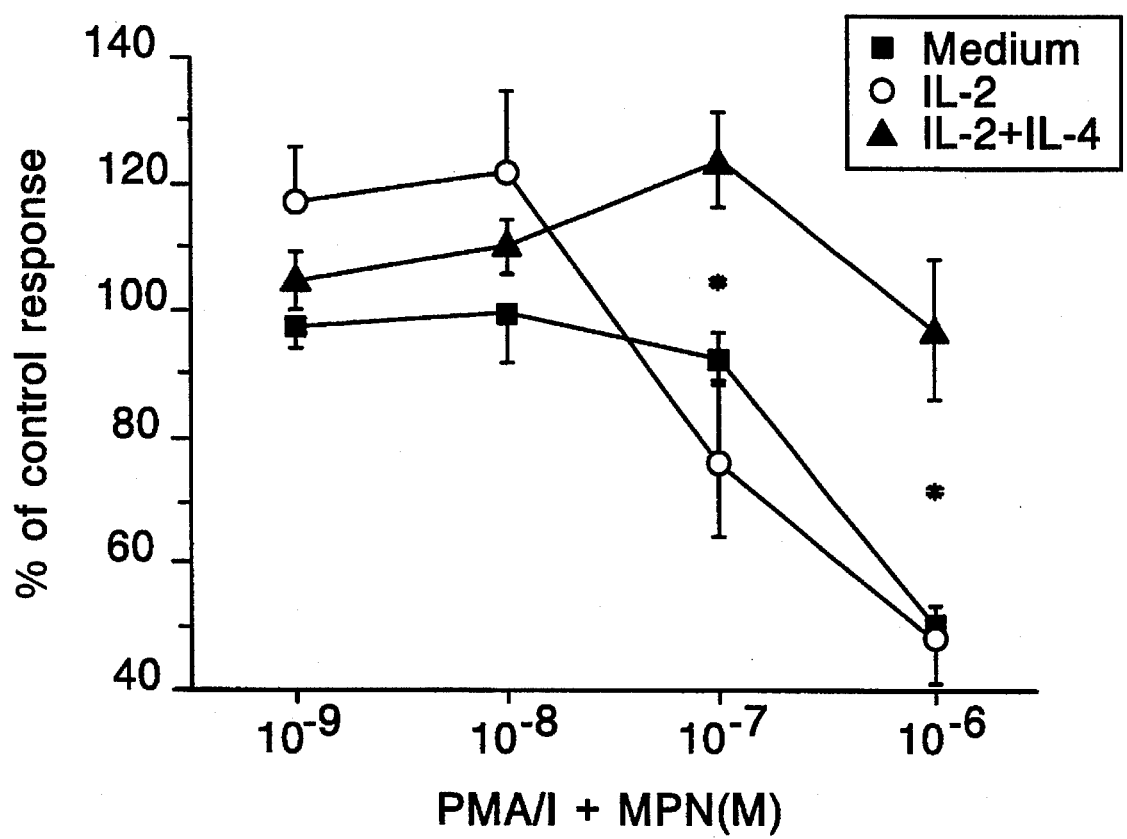
FIG. 3 illustrates the effect of the pre-incubation of PBMC with IL-2+IL-4 on PMA/I-induced proliferation.

Because IL-2+IL-4 preincubation resulted in an increase in GR number as well as a reduced binding affinity for glucocorticoids, the net functional effect of this pretreatment was studied. PBMC from four normal donors were preincubated in the absence and presence of IL-2+IL-4, or IL-2 alone, for 48 hours and then subsequently stimulated with PMA (0.01 μM) and I (0.05 μM) in the presence and absence of MPN ranging in concentration from $10^{-6}$ to $10^{-9}$M for another 72 hours. As summarized in FIG. 3, the preincubation of PBMC with combination IL-2+IL-4, but not IL-2 alone, resulted in a significantly decreased inhibitory effect of MPN on PMA/I-induced proliferation when compared with preincubation with medium alone. A significant dose-dependent inhibition of proliferation was noted with culture medium preincubation when compared with combination IL-2+IL-4 alone, especially at concentrations of $10^{-6}$M (p=0.009) and $10^{-7}$M MPN (p=0.009, ANOVA).

Mean control responses in the absence of MPN were 66,800 cpm for cells preincubated with IL-2+IL-4 and 51,200 cpm for cells incubated in medium alone after 72 hours of incubation. Each point represents the mean±SEM. Thus, despite the increased GR sites per cell, the net effect of IL-2+IL-4 preincubation was a functional resistance to MPN.

Localization of IL-2+IL-4 effect on GR-binding affinity to T cells

Figure 4A:
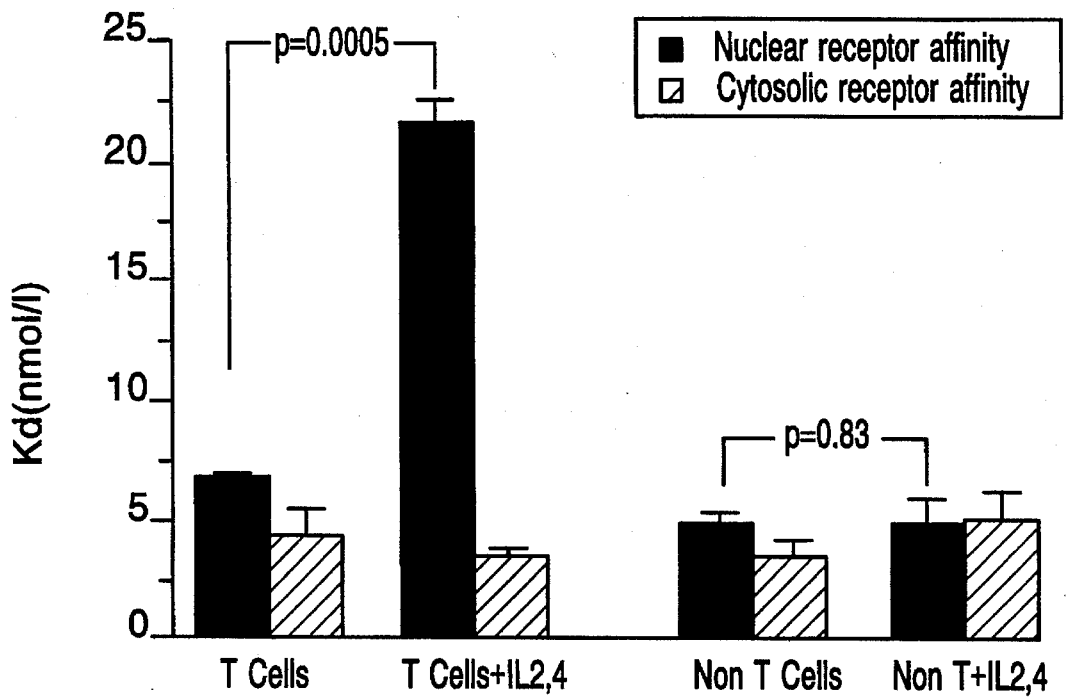
FIGS. 4A and B illustrates the measurement of glucocorticoid receptor number and binding affinity in fractionated T and non-T cell populations.
Figure 4B:
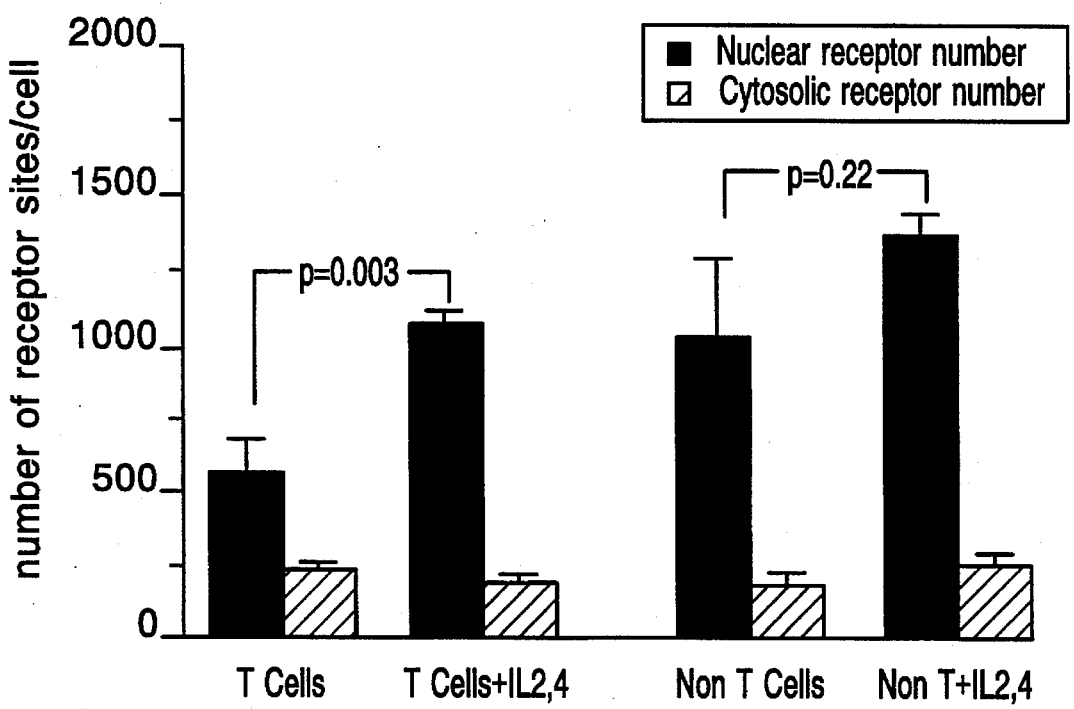

To determine whether the changes observed in GR-binding affinity and number of receptor sites per cell could be attributed to a specific mononuclear cell subpopulation, T cells and non-T cells were fractionated. Both cell populations were then separately stimulated with IL-2+IL-4 (FIG. 4). Significant reduction in GR-binding affinity was only observed in the T cell nuclear GR population after incubation (p=0.0005) with the combination of IL-2+IL-4 for 48 hours. No change in cytosolic GR-binding affinity was noted in either cell population (T cells, p=0.53; non-T cells, p=0.22). Although the non-T cell population demonstrated no change in nuclear $K_d$ (p=0.83), an increase in nuclear GR number was observed in both cell populations after incubation with IL-2+IL-4 but was only significant in the T cell population (p=0.03). There was no significant difference in the base line number of receptor sites per cell between T cells and non-T cells (p=0.13). Each bar represents the mean±SEM.

Effect of cytokine incubation on PBMC GR from SR asthmatics

Figure 5:
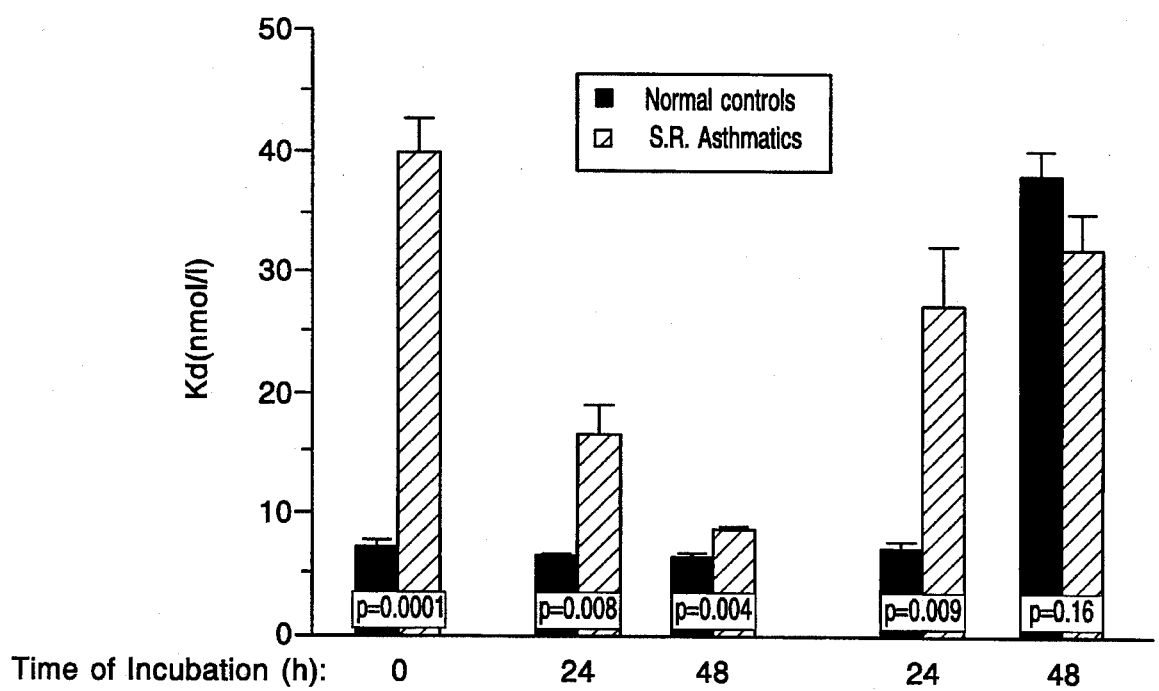
FIG. 5 illustrates the measurement of glucocorticoid receptor binding affinity in PBMC isolated from steroid-resistant patients and normal subjects.

Freshly isolated PBMC from four patients with SR asthma (time, 0 hours) were found to have a significantly reduced GR-binding affinity compared with four normal subjects (p=0.0001, unpaired t-test) (FIG. 5). GR-binding parameters were then measured after incubation of PBMC from SR asthmatic and normal subjects in the absence and presence of IL-2 (50 U/ml)+IL-4 (50 U/ml) for 24 and 48 hours. In normal subjects, PBMC incubated with combination IL-2 (50 U/ml)+IL-4 (50 U/ml) demonstrated no change in GR-binding parameters at 24 h, however, there was a significant increase (p=0.001) in GR $K_d$ and receptor sites per cell at 48 hours. In contrast, when PBMC from patients with SR asthma were incubated in medium alone they showed a significant reduction in GR $K_d$ within 24 hours (p=0.008 at 24 hours and p=0.004 at 48 h, paired t-test) of incubation with GR $K_d$ comparable with normal subjects by 48 hours. However, the reduced GR-binding affinity in PBMC from SR asthmatics was sustained in culture over the 48 hour period when their cells were incubated in the presence of IL-2+IL-4. Statistical difference between normal subjects and SR asthmatics is indicated in the corresponding square. Each bar represents the mean±SEM.

In the present study, alterations were induced in GR-binding affinity by incubating PBMC from normal donors with the combination of IL-2+IL-4 for 48 hours. The decreased PBMC GR-binding affinity induced by IL-2+IL-4 was similar to binding parameters observed in patients with SR asthma. IL-2+IL-4 did not induce lymphocyte proliferation, nor was there any change in the proportion of CD4 and CD8 cells over this 48 hour time period. Furthermore, incubation with IL-2 alone or IL-4 alone had no effect on GR binding. Thus, it appears that preincubation with the combination of IL-2+IL-4 together was an absolute requirement to induce an effect on GR-binding affinity.

Without being bound by theory, cytokines are believed to induce decreases in GR-binding affinity and may relate to the marked difference between the nuclear and cytosolic GR-binding parameters of PBMC treated with combination IL-2+IL-4. GR changes its structure and/or conformation when translocated between the nucleus and cytosol. The unliganded cytoplasmic GR can be a heteromer composed of a single steroid-binding and DNA-binding subunit and two 90-$K_d$ heat-shock proteins. The binding of glucocorticoid to its receptor results in the dissociation of the 90-$K_d$ heat-shock protein subunits and exposure of the DNA binding site on the receptor. This activated GR complex then translocates into the nucleus and regulates transcription by binding to specific DNA sequences, called glucocorticoid-responsive elements. The induction or repression of GR target genes ultimately results in the altered expression of glucocorticoid-regulated proteins. This latter action can be mediated via interaction of the modulatory domain of the GR with transcriptional factors, such as AP-1. Overexpression of AP-1 can interfere with the function of the modulatory domain of the GR. The nuclear localization of the GR defect induced by IL-2+IL-4 can occur because cytokines can induce elevated AP-1 levels.

BAL cells from atopic asthmatics have increased levels of mRNA for IL-2 and IL-4 but not IFN-γ. This pattern of cytokine production would be consistent with a predominant Th2-type T cell population in the lung. PBMC from SR asthmatics revert to a normal GR-binding affinity within 48 hours when cultured in the absence of cytokines, indicating that the alteration in GR-binding parameters is reversible. However, the abnormal GR-binding parameters in PBMC from SR asthmatics are sustained when incubated with combination IL-2+IL-4.

In addition, IFN-γ inhibited the PBMC GR alterations induced by IL-2+IL-4. This is consistent with the observation that a functional antagonism exists between IL-4 and IFN-γ. IL-4 enhances Th2 cell differentiation and cytokine production. In contrast, IFN-γ favors Th1 cell differentiation and cytokine production, inhibits IL-4 induced IgE synthesis, and selectively inhibits Th2 cell function and proliferation.

The opposing effects of IL-2+IL-4 and IFN-γ can have significant implications for future directions in the treatment of SR inflammatory disorders, such as asthma, or collagen-vascular diseases characterized by activated T cells. Steroid "resistance" in such conditions may be maintained or result from the local secretion of cytokines, such as IL-2 and IL-4 or other yet to be identified cytokines, in the inflamed tissues. The present study provides additional support for the investigation of cyclosporin A and other T cell modulators that down-regulate cytokine secretion in the treatment of SR inflammatory disorders.

Experiment 2—GR binding defects are associated with cytokine driven inflammation.

A group of 12 asthmatic patients who required a short course of high dose oral glucocorticoid (GC) (either prednisone 30 mg, n=10 or medrol 24 mg, n=2, administered twice daily) secondary to poor asthma control (significant dipping in morning $FEV_1$, nocturnal awakening with shortness of breath or wheezing despite optimal oral and inhaled bronchodilator therapy) were recruited from the outpatient clinic (n=2) or the adolescent inpatient unit (n=10) at National Jewish Center for Immunology and Respiratory Medicine to participate in the study. All subjects met the ATS criteria for asthma and had documented reversible airflow obstruction (20% improvement in $FEV_1$ in response to inhaled $\beta_2$-agonists). All subjects were on routinely administered inhaled β-agonists and inhaled GCs. In addition, 11 of the subjects were on theophylline and 8 were on maintenance oral GC therapy (daily or alternate day). Patients were excluded from the study if they had any other medical condition or had a recent history (within 6 weeks) of respiratory tract infection.

Study Design:

All subjects underwent an initial physical exam, had skin prick skin tests to major aeroallergens, and had blood drawn for evaluation of GR binding analysis, sIL-2R, ECP, IL-5 levels. In addition, baseline AM pre-bronchodilator spirometry and body box plethysmography was performed. All patients were then given 20 to 30 mg of prednisone or the equivalent dose of methylprednisolone for 7 to 10 days. Upon completion of the GC burst, repeat AM pre-bronchodilator spirometry was performed, and blood drawn for repeat GR binding analyses, sIL-2R, ECP, and IL-5 levels.

GR Binding Assay

PBMC's were isolated as described generally in Experiment 1. All blood samples were collected between 7:30 and 8:30 AM with at least a 24 hour interval between the analysis and oral steroid administration. GR binding studies using $^3$H-dexamethasone were performed as described generally in Experiment 1.

Measurement of sIL2R, ECP, IL-5 Levels

Blood was obtained in serum separator tubes which were incubated at room temperature for 60–120 minutes prior to centrifugation at 2,000 rpm for 10 minutes. The serum was separated, and aliquots of 0.5 ml were frozen at −20° C. until used. Soluble IL-2 receptor levels were performed using a commercially available enzyme immunoassay kit (T Cell Diagnostics, Cambridge, Mass.) according to the manufacturers instructions. The detection limit of this assay is approximately 50 U/ml, and the intra- and inter-assay variation coefficients were ≦3.5% and 6%, respectively.

ECP levels were determined using the Pharmacia CAP System ECP fluorescence enzyme immunoassay (FEIA) (Pharmacia Diagnostics AB, Uppsala, Sweden) according to the manufacturers instructions. Briefly, 50 µl of the test serum and ECP standards were added to Immunocaps covalently coupled to anti-ECP monoclonal antibody (Mab) (murine) and incubated for 30 minutes. The samples were washed prior to incubation (150 min) with the anti-ECP Mab coupled to β-galactosidase. After washing, the samples were incubated with 4methylumbelliferyl-β-D-galactoside for 10 minutes. After stopping the reaction, the fluorescence of the eluate was measured and the absorbances of the serum samples compared to the standard curve. The detection limit of the assay is <0.5 µg/l, and the intra- and inter-assay variation coefficients were ≦7% and 8%, respectively.

IL-5 levels were performed using a sandwich enzyme linked immunoassay. Briefly, microtiter plates were coated overnight with a murine anti-IL-5 Mab (Pharmingen). After washing, the plate was blocked with 200 µl of 3% bovine serum albumin (BSA) for 3 hours. The plate was washed and 100 µl of the serum samples and human rIL-5 (Genzyme) standards (19.5 to 2500 pg/ml) were added and incubated at 4° C. overnight. The plate was washed again and 100 µl of biotinylated anti-IL-5 secondary Mab (Pharmingen) added. After a 45 minute incubation, the plates were washed and 100 µl of an avidin-peroxidase solution was added to each well. After a 30 minute incubation, the absorbance was read in a Beckman spectrophotometer at 405 nm with the absorbances of the serum samples compared to the standard curve.

Statistical analysis

Differences between the pre-GC burst and post-burst values were tested using the student's paired t-test. To normalize the distribution of the serum ECP and sIL-2R results, logarithmic transformation of individual values was performed with the data expressed as the geometric means±S.E.M. To test for correlation between variables, Pearson's correlation coefficient was used.

TABLE 3

Clinical Details of Patients Studied
Clinical and Physiologic Response
The study subjects had asthma for 4–15 years (Table 3).

| Age | Gender | Duration of Asthma (yrs) | Oral GC dose (mg/day) | Inhaled GC dose (µg/ml) | Atopic status | FEV1 (% of predicted) | FEV1/FVC ratio |
| --- | --- | --- | --- | --- | --- | --- | --- |
| 12 | F | 10.5 | 20 | 1200 | Y | 68 | .57 |
| 14.5 | F | 13 | 20 | 5000 | Y | 63 | .63 |
| 17.5 | M | 13 | 10 | 3000 | Y | 65 | .6 |
| 15 | F | 4 | 15 | 1500 | Y | 82 | .67 |
| 14.8 | M | 14 | 15 | 1200 | N | 72 | .57 |
| 15.5 | M | 5.5 | 40 | 2250 | Y | 61 | .57 |
| 13 | F | 10 | 0 | 2000 | Y | 43 | .5 |
| 13.8 | M | 12.5 | 0 | 4000 | Y | 61 | .65 |
| 12 | M | 10 | 0 | 1600 | Y | 65 | .64 |
| 26 | F | 25 | 0 | 1600 | Y | 58 | .6 |
| 13.5 | M | 12.5 | 20 | 2000 | N | 81 | .65 |
| 17 | F | 15 | 40 | 3750 | Y | 66 | .6 |
| Mean ± SEM 15.4 ± 1.09 | | 12.1 ± 1.51 | 15 ± 4.13 | 2425 ± 356.8 | 10/12 | 65.4 ± 2.98 | 0.60 ± 0.014 |

At entry, all subjects were on high dose inhaled GC therapy (mean dose 2335±405 µg/day), and 8 of the 12 were on maintenance oral steroids (mean dose 15±4.1 mg/day). In addition, all subjects were on routinely administered inhaled bronchodilator therapy (at least 3 times daily) and all had been or were currently on theophylline. Baseline pulmonary function studies revealed evidence for hyperinflation (total lung capacity 120.1±4.5% of predicted, thoracic gas volume 133.2±5.6%), air-trapping (residual volume 226±23.5% of predicted), and airflow obstruction ($FEV_1$/forced vital capacity (FVC) ratio 0.61±0.02). All patients had a significant nocturnal component to their asthma and all except for two, were atopic as defined by two or more positive skin prick tests to common aeroallergens.

Figure 6B:
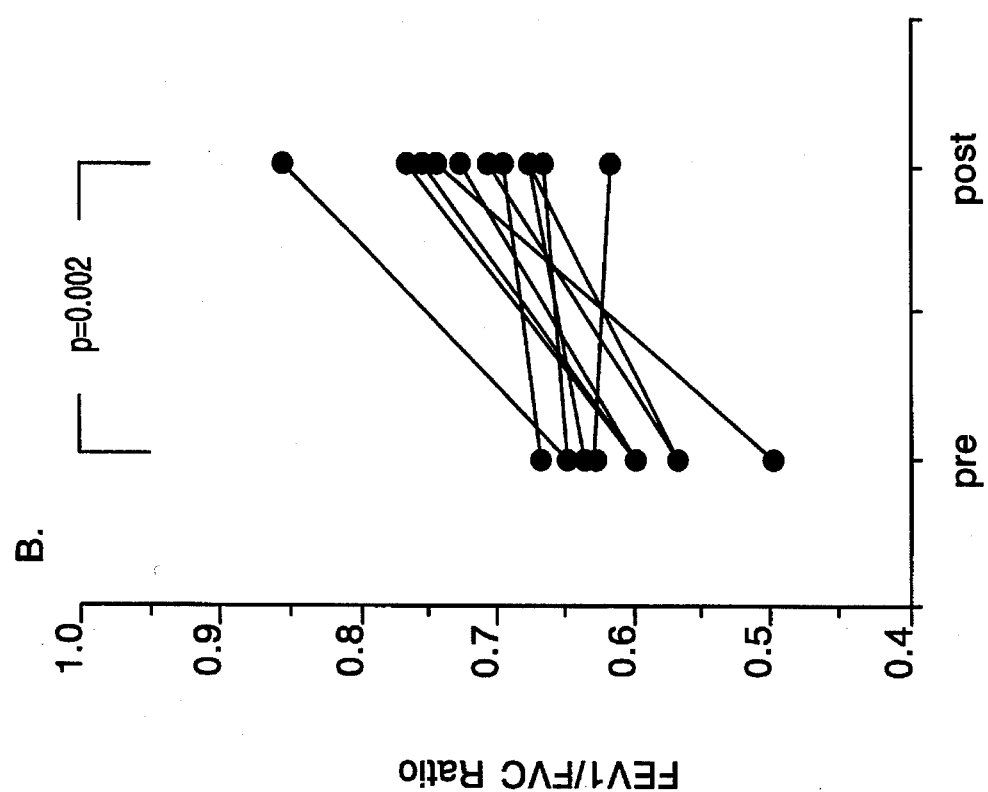
FIGS. 6A and B illustrates the effect of a course of glucocorticoid treatment on the $FEV_1$ and $FEV_1/FVC$ ratio values of asthmatic patients.
Figure 6A:
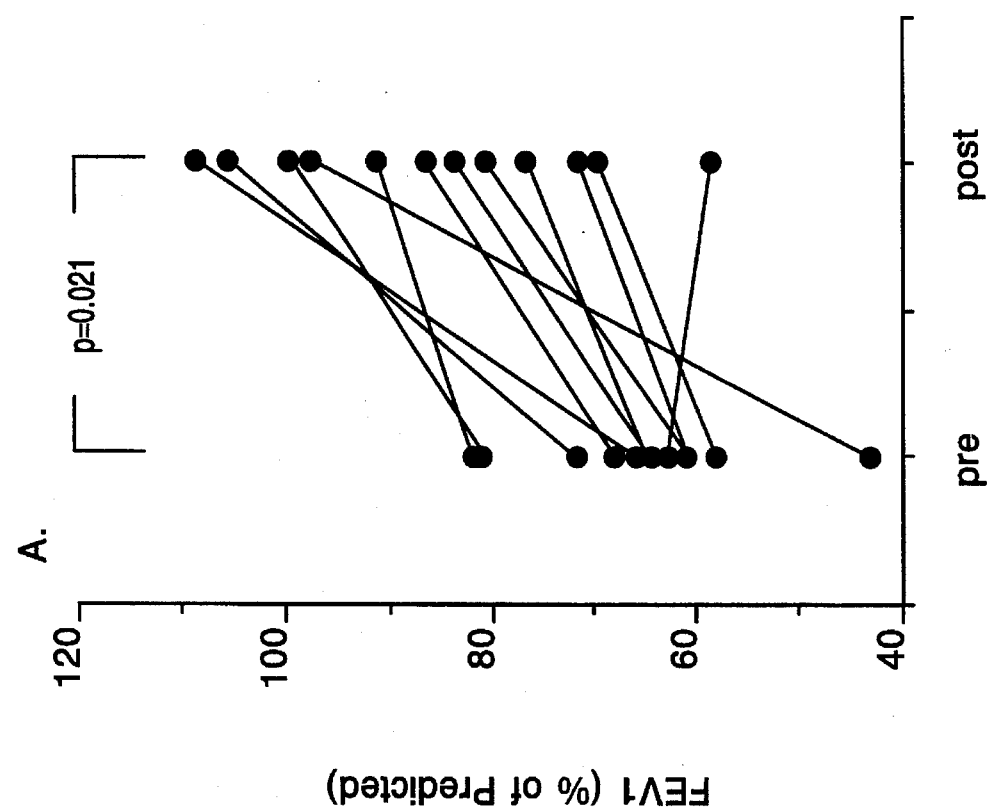

All subjects successfully completed the 7–10 day course of oral GC therapy with no adverse reactions associated with the GC treatment. Eleven of the 12 patients reported an improvement in their symptoms accompanied by a significant improvement (34.7±9.9%) in their AM pre-bronchodilator pulmonary function (mean $FEV_1$ 65.4±3.4% of predicted to 84.2±4.5%; p=0.021) as seen in FIG. 6A. In addition, there was a significant reduction of airflow obstruction as measured by the $FEV_1/FVC$ ratio (FIG. 6B, mean $FEV_1/FVC$ ratio 0.61±0.14 to 0.72±0.02; p=0.0016).

GR Analysis

As seen in Table 4, the mean baseline GR kd of the study group was found to be significantly elevated compared to a group of previously studied stable asthmatics and normal controls (Kd pre-burst 33.4±4.4 nM, stable asthmatics 21.0±1.7 nM, n=10; normal controls 7.8±0.4 nM, n=11).

response to GCs. There is a significant decrease in the GR binding affinity in a population of poorly controlled steroid dependent asthmatics. This defect in GR affinity was associated with significantly elevated serum levels of ECP and sIL-2R both of which serve as peripheral markers of allergic inflammation and immune activation. These abnormalities were found despite optimal asthma management which included high dose inhaled GC and in many cases oral GC therapy. Of interest, the mean daily inhaled GC dose of the

TABLE 4

| | Glucocorticoid Receptor Binding Affinity/Number | | | | |
|---|---|---|---|---|---|
| | Subjects Pre-GC Burst n = 12 | Subjects Post-GC Burst n = 12 | Normal Volunteers n = 11 | Steroid Sensitive Asthma n = 10 | Steroid Resistant Asthma n = 17 |
| Kd (nM) | 33.4 ± 4.4 | 14.9 ± 3.0 | 7.8 ± 0.4 | 21.0 ± 1.7 | 40.8 ± 3.4 |
| Receptor sites/cell | 7681 ± 1816 | 3238 ± 931 | 2592 ± 170 | 4633 ± 551 | 9674 ± 1188 |

Thus, the GR in the study group had a significantly lower binding affinity than either control group. In addition, the number of receptor sites per cell preburst were significantly elevated versus stable asthmatics and controls (preburst 7681±1816 versus stable asthmatics 4633±551 versus 2592 170 for normal controls).

Furthermore, as noted in FIG. 6a, the GC burst therapy was associated with a significant improvement in the GR binding affinity as manifest by a decrease in the GR Kd from 33.4±4.4 nM to 14.9±3.0 nM (p=0.0012). Accompanying the improved binding affinity was a significant decrease in the number of GR sites per cell (FIG. 6b, 7906±1597 to 3238±931 receptor sites/cell; p=0.007).

Serum sIL-2R, ECP, IL-5 Measurements

To determine whether the defect in GR binding affinity prior to and after prednisone paralleled serum markers of inflammation (ECP) and immune activation (sIL2R), ECP and sIL-2R levels were measured prior to and following the oral GC burst therapy. The mean pre-GC burst ECP level of 24.7 ng/ml for the study patients was found to be elevated compared to values previously reported in healthy adult controls (mean=4.4 ng/ml). In addition, a significant reduction in the mean serum ECP level was noted (FIG. 7A) following GC burst therapy with the geometric mean level falling from 18.8 ng/ml preburst to 9.72 ng/ml post-burst (p=0.0061).

Figures 7A, 7B:
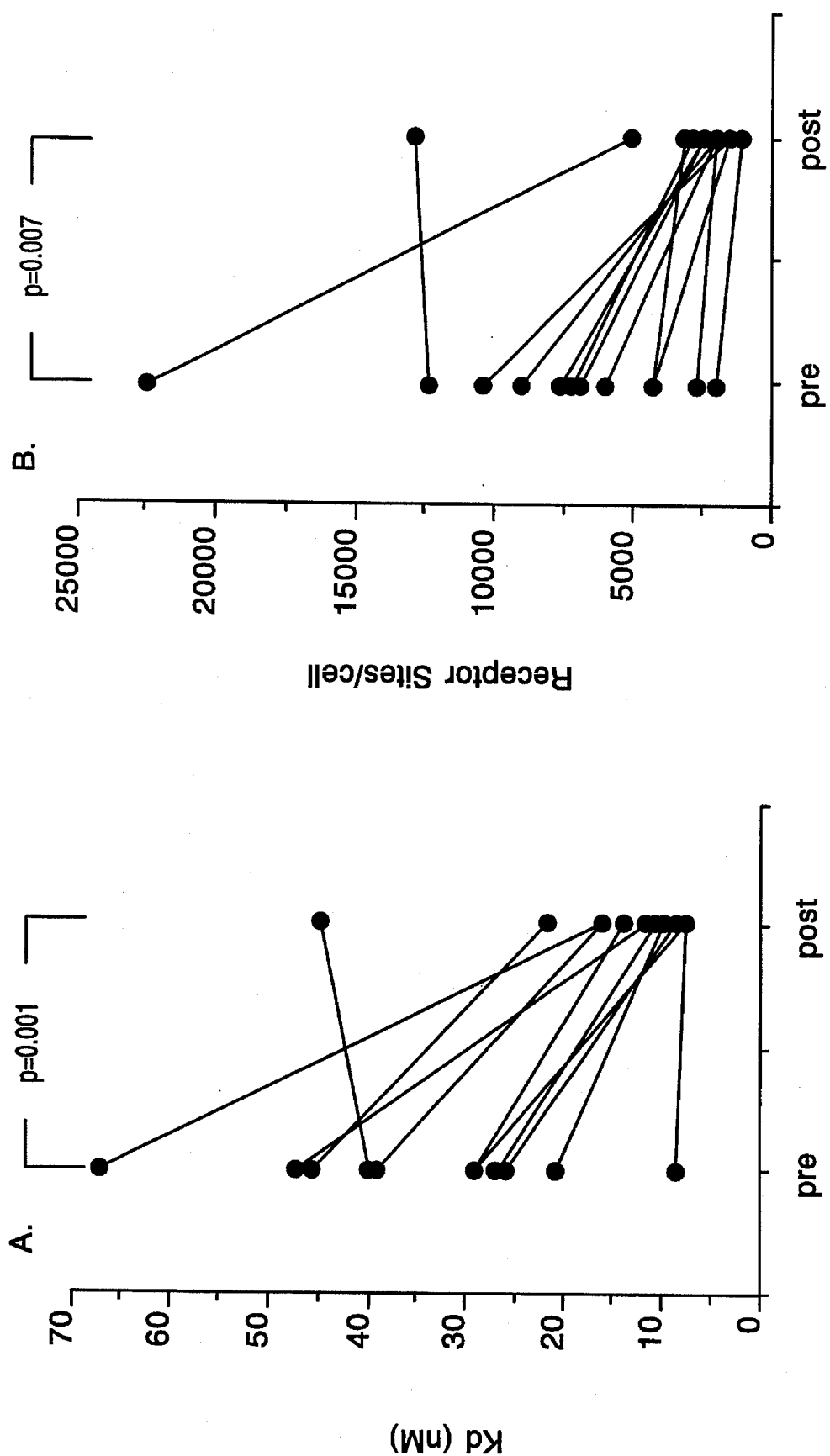
FIGS. 7A and B illustrates the effect of a course of glucocorticoid treatment on glucocorticoid receptor number and binding parameters.
Figure 8B:
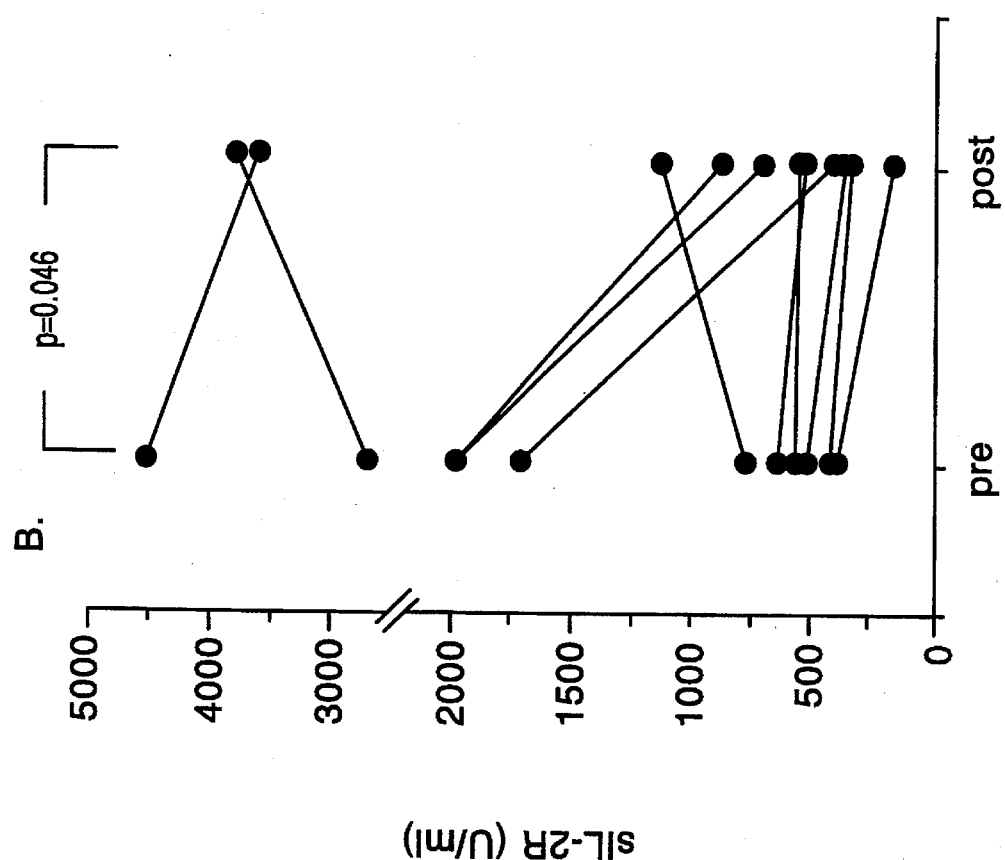
FIGS. 8A and B illustrates the effect of a course of glucocorticoid treatment on IL-2 receptor numbers and serum ECP in asthmatic patients.
Figure 8A:
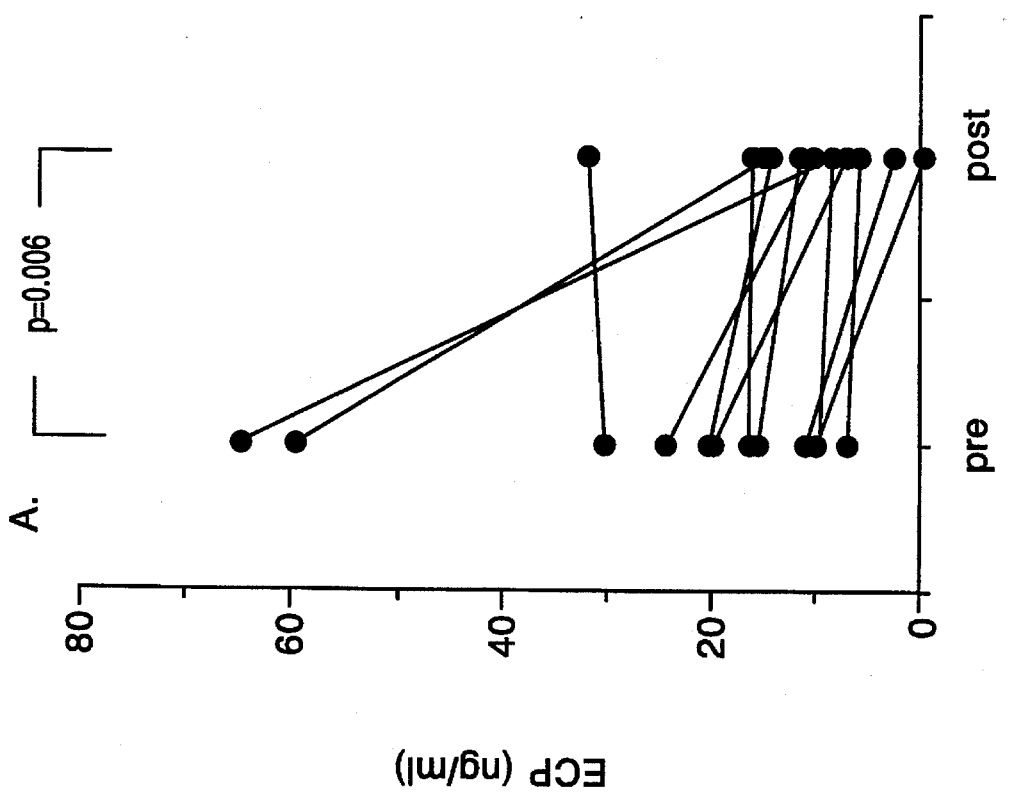

The study subjects were also found to have an elevated pre-GC burst sIL-2R level with a geometric mean of 101 1.6 U/ml (FIG. 7B). This value is greater than 2 standard deviations from the mean obtained from 50 healthy adult blood donors (mean=573, 2 standard deviations from the mean ≦919 U/ml) as reported by the manufacturer. Similar to that seen with serum ECP, a statistically significant reduction in the geometric mean sIL-2R level was noted following the GC burst therapy (101 1.6 versus 704.7 U/ml, p=0.046). As seen in FIG. 7b, there was a wide range of values from normal to extremely elevated levels. In addition, in some cases the levels actually increased following the GC burst therapy despite improvement in spirometry and GR binding affinity. The pre-GC burst sIL-2R appeared to be a good predictor of the severity of airflow limitation in that a significant correlation was seen between pre-GC burst $FEV_1$ (% of predicted) and sIL-2R levels (r=0.64, p=0.026).

The present study provides further insight into the mechanisms involved in the pathogenesis of poorly controlled asthma, and how this process may potentially alter the study subjects was several times greater than the recommended pediatric dose.

The short course of high dose oral GC burst therapy was associated with a favorable clinical and spirometric response in two of the twelve study subjects with a mean improvement in their AM pre-bronchodilator $FEV_1$ of 34%. Accompanying this improvement in pulmonary function, was a substantial increase in GR binding affinity as manifested by a significant decrease in the Kd. The data supports the concept that the improvement in the baseline diminished GR binding affinity was associated with the GCs modulation of on-going airway inflammation.

Without being bound by theory, it is believed that the improvement in GR binding affinity following GC burst therapy can likely result from the inhibition of pro-inflammatory cytokines and mediators which may be important not only in the maintenance of airway inflammation but also in the generation of the GR binding defect. Oral steroids may also be effective in the treatment of asthma. In vitro, GCs can be effective in inhibiting the expression of several cytokines including, for example, IL-1, IL-2, IL-3, IL-4, and IL-5. In addition, by virtue of their ability to up regulate lipocortin, GCs inhibit the production of arachidonic acid derived proinflammatory molecules such as $LTC_4$, and PAF. Oral GC therapy can also inhibit the influx of non-resident inflammatory cells into sites of allergic inflammation.

ECP levels were found to be elevated in patients having poorly controlled asthma. ECP can be used as a peripheral marker of inflammation because ECP is released specifically by activated eosinophils and is toxic to respiratory epithelium in vitro. ECP levels can correlate with disease severity. However, ECP levels do not always correlate with the occurrence of inflammation sIL-2R levels were significantly elevated. The sIL-2R level is age dependent with highest levels noted in infancy. These levels fall during childhood reaching adult levels by 10 years. Since the youngest study subject was 12 years old, it is unlikely that the elevated levels are due to maturational effects. Rather, the elevated levels most likely reflect on-going immune activation despite anti-inflammatory treatment with high dose inhaled and often oral GC therapy. Similar to ECP levels, a substantial reduction in the sIL-2R geometric mean was noted following the GC burst therapy. In addition, a substantial correlation was noted between pre-GC sIL-2R levels and baseline $FEV_1$ values (both raw values and % of predicted). However, sIL-2R levels do not always correlate with the occurrence of inflammation.

Experiment 3—GR binding abnormalities are reversible in poorly controlled asthmatics using prednisone therapy.

10 poorly controlled asthmatics received a 7–10 day course of high dose oral Prednisone (20–30 mg po bid). Following prednisone treatment, PBMC's were obtained as generally described in Experiment 1 and the whole cell GR number (sites/cell) and binding affinity (Kd, nmol/l) were determined using techniques generally described in Experiment 1. In addition, spirometry and serum ECP levels were measured pre- and post-Prednisone treatment. As shown in Table 5, the poorly controlled asthmatics had significantly elevated baseline values for GR number and Kd compared to normal controls (Kd 7.8±0.4, GR number 259±170, n=11).

TABLE 5

| Parameter | Pre-Pn | Post-Pn | p value |
|---|---|---|---|
| GR binding Affinity (Kd) | 33.3 ± 5.0 | 15.8 ± 3.6 | 0.005 |
| GR Number (sites/cell) | 8029 ± 1875 | 3575 ± 1094 | 0.024 |
| ECP (μg/l) | 16.1 ± 1.9 | 10.8 ± 1.2 | 0.045 |
| $FEV_1$ (% predicted) | 63.8 ± 3.2% | 82.6 ± 4.4% | 0.008 |
| $FEV_1$/FVC Ratio | 0.60 ± 0.02 | 0.70 ± 0.01 | 0.014 |

These values decreased significantly towards normal values following the Prednisone burst. Accompanying this change, there was a substantial decrease in the serum ECP levels (normal value 5.8 μg/l), and a significant improvement in pulmonary function post Prednisone burst. The data are expressed as means±SEM, p values determined using a paired, 2 tailed t-test.

The data indicate that GR binding abnormalities can be reversible in vivo following a course of high dose Prednisone therapy and are probably not caused by prior treatment with Prednisone. Without being bound by theory, it is believed that the normalization of GR defects results from suppression of inflammation, contributing to increased GR binding affinity and resulting in clinical improvement.

Experiment 4—SR asthmatics demonstrate alternate GR binding parameters and GR concentrations.

Methods

Patients with a diagnosis of asthma, based on American Thoracic Society criteria, were selected for evaluation. The patients had a morning prebronchodilator $FEV_1$<70% of predicted values and a ≧15% increase in $FEV_1$ after two inhalations of albuterol (90 μg per actuation). Patients were excluded if they had evidence for other types of lung disease, pregnancy, suspected noncompliance with medical care, or concurrent therapy with medications that alter glucocorticoid metabolism, such as anti-convulsants or erythromycin. A complete set of pulmonary function tests with lung volume, methacholine bronchial challenge, and diffusion capacity/total lung capacity ratio were obtained if the diagnosis of asthma required confirmation.

Patients were classified as SS or SR based on their prebronchodilator morning $FEV_1$ and their response to a course of oral prednisone. Asthmatic patients were defined as SR if they failed to improve their morning prebronchodilator $FEV_1$ by ≧15% after a 1 week course of prednisone at a minimum oral dose of 40 mg/day. Patients were classified as SS if they had an increase in baseline $FEV_1$ of 30% or greater. All SR asthma patients had glucocorticoid pharmacokinetic studies to exclude those patients with an abnormality in prednisone absorption or metabolism.

PBMC's were isolated as described generally in Experiment 1. All blood samples were collected between 7 and 8 a.m., before medications and at least 24 hours after any oral glucocorticoid therapy. Glucocorticoid binding assays were performed as generally described in Experiment 1.

Reversibility and cytokine incubation protocols.

PBMC from normal donors and SR asthma patients were isolated and resuspended at a concentration of $1\times10^6$ cells/ml in RPMI 1640 medium (Gibco Labs.) containing 10% heat-inactivated fetal calf serum (Hyclone Labs., Logan, Utah). Cells were incubated in the absence and presence of IL-2 (50 U/ml; Cetus Corp., Emeryville, Calif.) and/or IL-4 (50 U/ml; obtained from Schering-Plough Research Institute) for 48 hours at 37° C. in 5% $CO_2$. PBMC were then analyzed for GR binding parameters.

Patient characteristics

Patient characteristics are summarized in Table 6.

TABLE 6

| PARAMETER | SS Asthma Patients | SR Asthma Patients |
|---|---|---|
| Number of subjects | 12 | 17 |
| Age (yr)* | 24 | 24 |
| Sex (m/f) | 8/4 | 12/5 |
| $FEV_1$ before BD (% predicted)* | 47 | 58 |
| $FEV_1$ after BD (% predicted)* | 69 | 74 |
| $FEV_1$ after steroid burst | 82 | 57 |
| Duration of asthma (yr)* | 16 | 19 |
| Inhaled steroids (yes/no) | 6/6 | 14/3 |
| Systemic steroids (yes/no) | 0/12 | 12/5 |
| Systemic steroid doses▼ | N/A | 24 |
| Atopy (positive/negative) | 11/1 | 16/1 |

*Mean value of patients before burst.
▼Mean daily prednisone dose in milligrams. BD. bronchodilator dose.

SR and SS asthmatics were similar for all parameters with two exceptions. First, although the SR asthmatics had a higher baseline $FEV_1$ (P=0.025) before the prednisone course as compared with the SS asthma patients, their $FEV_1$ after treatment with prednisone was significantly lower than SS asthmatics (P=0.0001). Second, 12 of the 17 SR asthma patients received maintenance oral prednisone (mean daily dose=24 mg) at the time of their GR assay as compared with none of the SS asthma patients. The majority of SR patients (Type I SR asthma, see below) developed cushingoid features during prednisone therapy. In contrast, one of the patients subsequently labeled Type II SR asthma (see below) maintained a normal plasma cortisol concentration (12 μg/dl) and did not develop cushingoid features despite continuous treatment with oral prednisone (20 mg daily). The other Type II SR asthma patient did not receive maintenance prednisone therapy because of poor clinical response.

Figure 9:
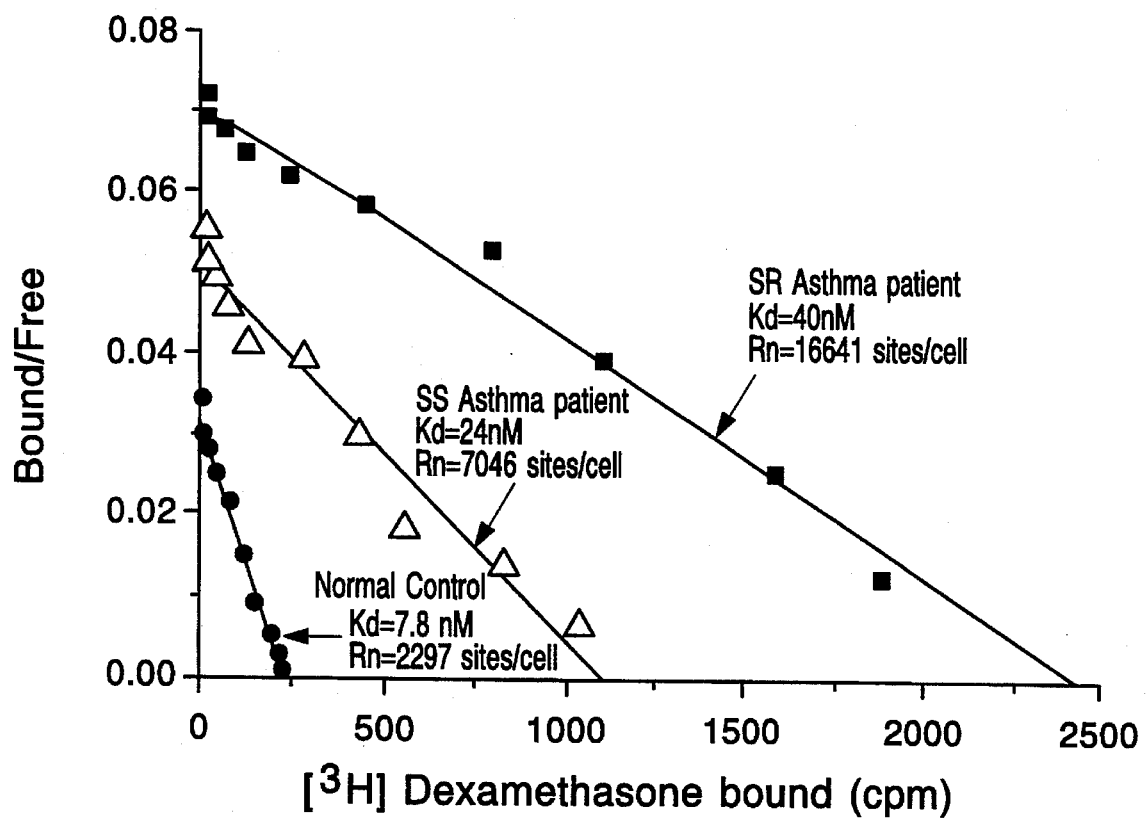
FIG. 9 illustrates a scatchard plot analysis if [³H]dexamethasone radioligand binding data of PBMC from a normal donor, a steroid-sensitive asthmatic and a type 1 steroid-resistant asthmatic.

PBMC glucocorticoid receptor binding parameters in steroid-resistant asthma patients Representative Scatchard plots are presented in FIG. 9 from PBMC [$^3$H]dexamethasone radio-ligand binding data from a normal donor, a patient with SR asthma, and a patient with SS asthma. PBMC GR binding parameters were examined in three study groups: 17 SR asthma patients, 12 SS asthma patients, and 12 normal nonasthmatic controls. Each study group showed distinctive binding patterns for their respective nuclear GR. Nonspecific [$^3$H]dexamethasone binding was low in all three study groups (2.6±0.5 versus 5.2±1.6 versus 3.5±1.0, respectively, for normals, SS asthmatics, and SR asthmatics) and no significant difference (P=0.2, ANOVA) was observed in nonspecific binding among the three groups.

As described in FIG. 10, 15 of the 17 patients with SR asthma had a significant increase in their GR Kd, i.e., a decrease in binding affinity for glucocorticoids, and an increased GR number in the nuclear fraction of their PBMC when compared with normal subjects or SS asthma patients (P=0.0001, ANOVA). These are characteristics of Type I SR asthma. Two other patients with SR asthma had normal GR $K_d$ values but a markedly decreased number of GR binding sites per cell, i.e., <3 SD below the normal range, compared with all other groups. Both patients were examined in the absence of maintenance prednisone therapy. These 2 patients have SR asthma classified as Type II SR asthma. SS asthma patients also had a decreased GR binding affinity as compared with normals. Their increased GR $K_d$ and GR number were significantly less than those observed in the SR asthma group but significantly more than the normal control group (P=0.0001, ANOVA). Patients with SR asthma or SS asthma did not have any significant abnormality in cytosolic GR $K_d$ or GR number (Table 7).

Figure 12A:
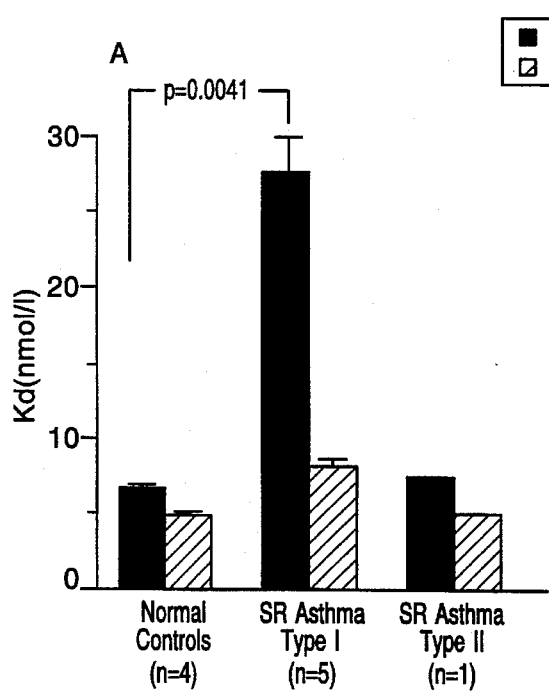
FIGS. 12A and B illustrates the measurement of glucocorticoid receptor number and binding affinity in fractionated T and non-T cell populations from steroid-resistant patients.
Figure 12B:
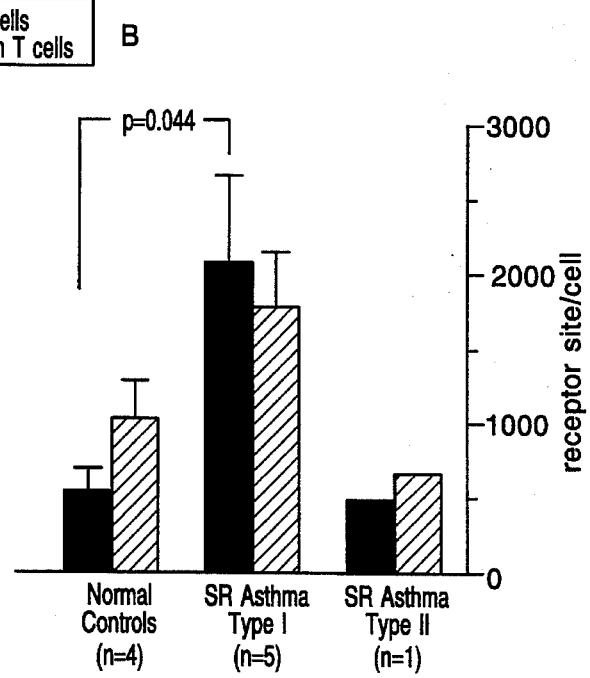

To determine whether the altered GR binding parameters were restricted to specific subsets of mononuclear cells in the two subtypes of SR asthma patients, the GR binding parameters in the patient's T cell and non-T cell subpopulations were analyzed. A fourfold significant increase (P=0.0009) in T cell nuclear GR $K_d$ over non-T cells was observed in the population of Type I SR asthma patients as compared with a small but significantly (P=0.02) greater T cell nuclear GR $K_d$ over non-T cells in normal controls (FIG. 12). The T cells from Type I SR asthma patients also had a significantly higher GR $K_d$ (P=0.0001) and GR number (P=0.046) than T cells from normal controls. In contrast, the abnormally low GR number observed in a Type II SR asthma patient was not limited to T cells but was also present in non-T cells as well (FIG. 12). Insufficient cells were available from the second Type II SR asthmatic for mononuclear cell subset analysis.

TABLE 7

| | Glucocorticoid Receptor Binding Parameters | | | |
|---|---|---|---|---|
| | Nuclear binding sites | | Cytosolic binding sites | |
| Study group | $K_d$ nM | GR sites/cell | $K_d$ nM | GR sites/cell |
| Normal controls (n = 12) | 7.94 ± 0.37* | 2514 ± 173* | 4.34 ± 0.50 | 290 ± 39 |
| Asthma patients (n = 12) steroid sensitive | 21.6 ± 2.10* | 6130 ± 891* | 8.53 ± 2.13 | 460 ± 124 |
| Asthma patients (n = 15) steroid resistant - Type I | 42.1 ± 3.07* | 9807 ± 1146* | 6.81 ± 1.50 | 383 ± 87 |
| Asthma patients (n = 2) steroid resistant - Type II | 7.35 ± 0.78 | 572 ± 64 | 5.35 ± 0.40 | 253 ± 14 |

Values are ± SEM.
*Significantly different from other two groups (P = 0.0001, ANOVA) Type II SR asthma patients were not included in statistical analysis.

Figure 11B:
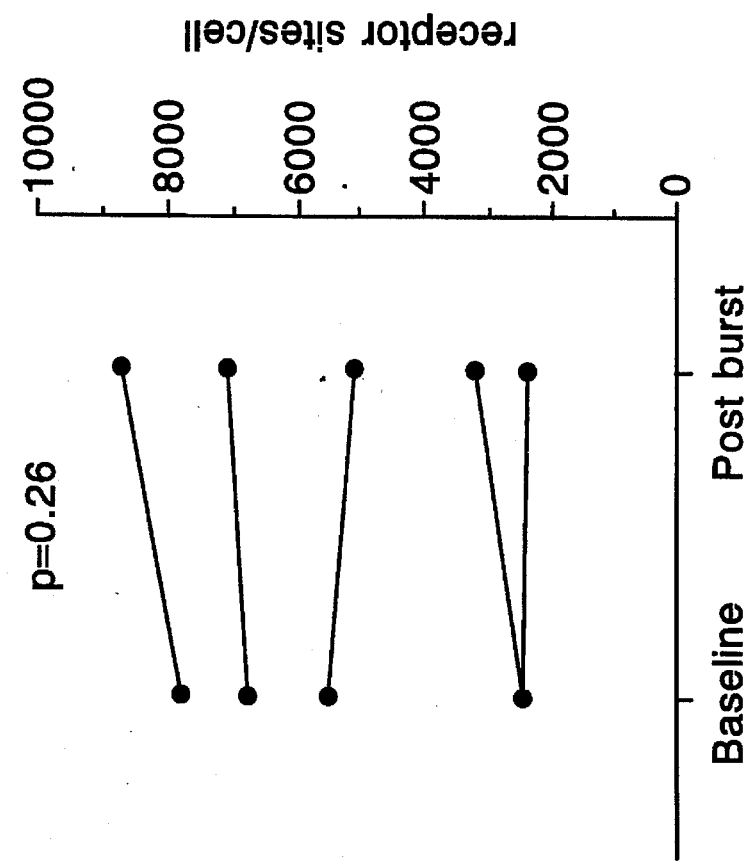
FIGS. 11A and B illustrates the effect of a one-week course of oral prednisone (40 mg/day) on glucocorticoid receptor binding parameters in 5 steroid-sensitive patients.
Figure 11A:
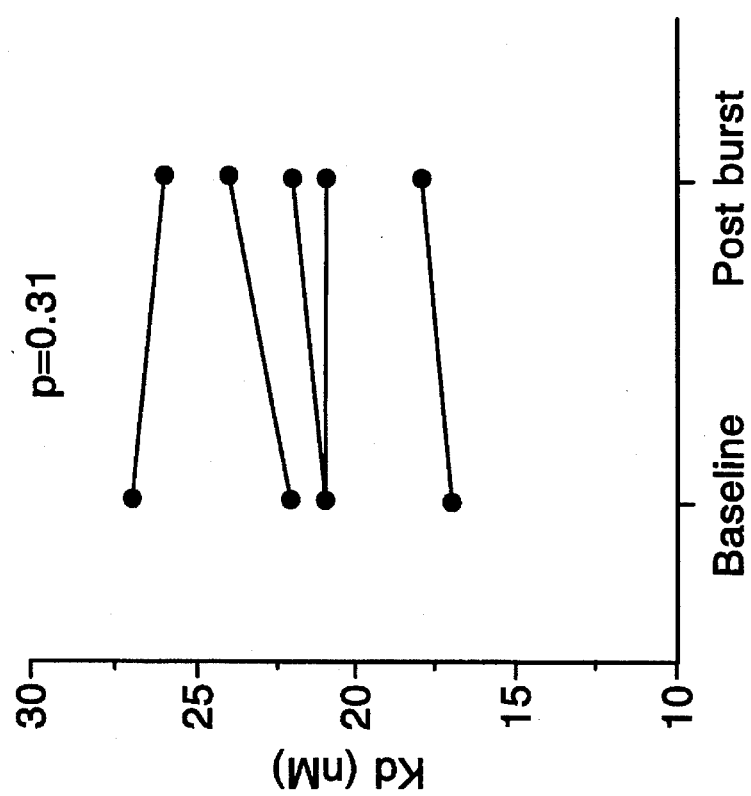

Since 12 of the 17 patients with SR asthma received oral prednisone (mean daily dose=24 mg) at the time of their GR assay, the effect of systemic steroids on GR binding parameters was examined. Three approaches were used. First, GR binding parameters of PBMC from five SS asthma patients was measured before and immediately after a 1 week course of 20 mg twice daily prednisone. No significant changes occurred in either GR number (P=0.26) or GR $K_d$ (P=0.31) after this 1 week course of high dose oral prednisone (FIG. 11). Second, PBMC from seven patients were assayed who were on 3–12 month protocols of 20–100 mg prednisone daily for treatment of other diseases associated with tissue inflammation (multiple sclerosis [n=1], pulmonary berylliosis [n=3], nummular eczema [n=1], chronic obstructive pulmonary disease [n=1], and interstitial lung disease [n=1]). None of these patients showed the degree of GR abnormality observed in the SR asthma patients. The GR number (5,591±361) and GR $K_d$ (22.9±1.40) of these seven patients were comparable with those of SS asthma patients and were significantly less than the Type I SR asthma patients (P=0.0001). Finally, the difference in GR binding parameters was examined between Type I SR asthma patients who did or did not receive maintenance oral prednisone therapy. Four of the Type I SR asthmatics were not taking oral steroids (FIG. 10). The PBMC still exhibited the same GR $K_d$ (40.8 nM) as the other 11 Type I SR asthmatics (GR $K_d$=42.6 nM) who received maintenance oral prednisone therapy. All of the above suggest that the significantly reduced GR binding affinity in Type I SR asthma is not induced by glucocorticoid therapy.

Figure 13A:
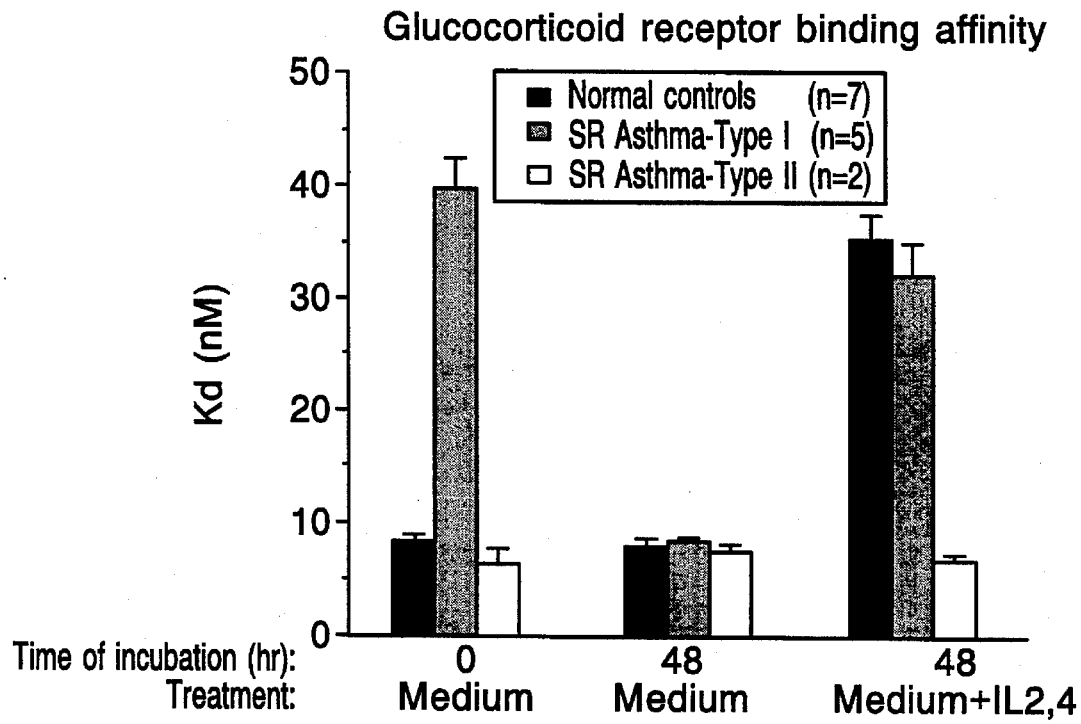
FIGS. 13A and B illustrates a time course of nuclear glucocorticoid receptor binding parameters in PBMC from type I and type II steroid-resistant asthma patients and normal subjects.
Figure 13B:
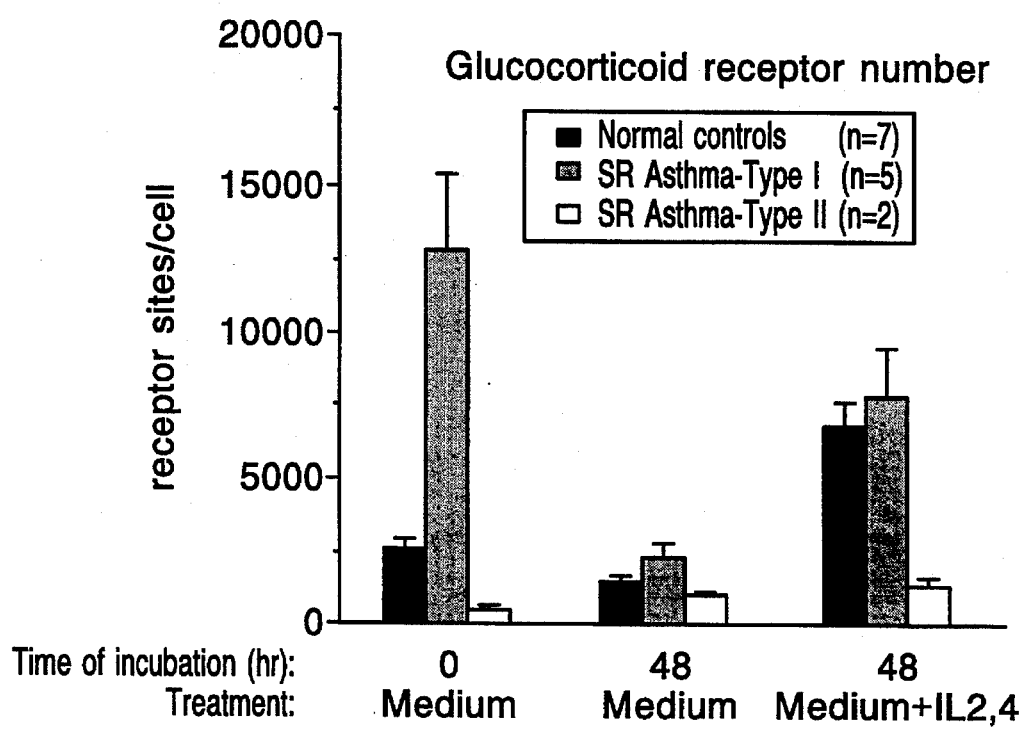

Localization of GR binding affinity defect to T cells in Type I SR asthma patients Effect of in vitro incubation on PBMC GR from SR asthmatics To determine whether the alterations in PBMC GR binding parameters from patients with SR asthma were reversible, GR binding was measured before and after incubation of PBMC in culture medium (FIG. 13). When PBMC from five patients with Type I SR asthma were incubated in medium alone they showed a significant (P=0.0001) change in GR binding with normalization of both GR $K_d$ and GR number after 48 hours of incubation as compared with values after immediate analysis. Incubation of PBMC from seven normal donors (FIG. 13) under similar culture conditions did not result in any significant change in either GR $K_d$ or GR number.

These data support the concept that the GR binding alterations in Type I SR asthma patients were acquired. Since asthma is associated with increased immune activation and cytokine secretion, the effects of IL-2 and IL-4, two cytokines reported to be increased in asthma, on GR binding parameters in patients with Type I SR asthma and normal donors was examined. When normal PBMC were incubated with the combination of IL-2 and IL-4, a significant increase was observed both in GR $K_d$ (P=0.0001) and in the number of GR sites per cell (P=0.001) at 48 hours as compared with values after immediate analysis. In contrast, the reduced GR binding affinity in PBMC from Type I SR asthmatics was sustained in culture over the 48 hour period when their cells were incubated in the presence of combination IL-2 and IL-4 (FIG. 13). Incubation of normal PBMC with IL-1, IL-5, and interferon-gamma for 48 hours, as compared with culture medium alone, did not induce a substantial elevation in GR $K_d$. Based on a minimum of three experiments, mean±SEM, GR $K_d$ after incubation with medium alone was 7.6±0.4, after IL-1 was 3.6±1.2, after IL-5 was 9.1±0.7, and after interferon-gamma was 6.2±0.4.

The effect of in vitro 48 hour incubation with media alone and with a combination of IL-2 and IL-4 on the two Type II SR asthma patients with low GR number was studied (FIG. 13). In contrast to the Type I SR asthma patients with elevated GR Kd and GR number, PBMC from these two patients did not demonstrate any changes in GR binding when incubated in culture medium alone. Furthermore, although the combination of IL-2 and IL-4 increased the number of GRs in normal PBMC, these cytokines had no effect on GR binding parameters from these two Type II SR asthma patients. Thus, it appears that the low GR number in Type II SR asthma patients is a primary irreversible defect, whereas the reduced GR binding affinity in Type I SR asthma patients is an acquired reversible defect.

These studies indicate that there are at least two mechanisms present in SR asthma patients. Type I SR asthma patients have an abnormally reduced GR binding affinity and an increased number of receptor sites per cell compared with normal population and SS asthma patients. The defect in Type I SR asthma PBMC GR binding can be limited to the T cell population. Conversely, SR asthma patients with the Type II binding abnormality have normal binding affinity with a markedly reduced number of glucocorticoid receptors per cell. An important distinction between these two types of SR asthma was that the GR defect in Type I SR asthma was reversible in culture but was sustained with the co-incubation of combination IL-2 and IL-4. In contrast, the binding defect in Type II SR asthma was irreversible and did not respond to co-incubation with combination IL-2 and IL-4. Furthermore, the PBMC GR defect in this latter form of SR asthma was not restricted to T cells.

Systemic glucocorticoid therapy is not responsible for the observed abnormalities in GR binding parameters because: (a) no significant change in GR binding parameters after 1 week of high dose "burst" prednisone in five SS asthma patients who were not receiving oral prednisone maintenance therapy; (b) that a disease control group receiving chronic high dose prednisone therapy did not show the same degree of abnormality in GR Kd as the Type I or GR number as the Type II SR asthmatics; and (c) Type I SR asthma patients who were not receiving oral prednisone had abnormal GR binding affinity in the same range as Type I SR asthma patients receiving oral prednisone maintenance therapy. Both the Type II SR asthmatics were studied while not taking systemic glucocorticoids.

The SS patients also have reduced GR binding affinity as compared with normal donors but less than that observed in Type I SR asthma patients. These data are of particular interest because they suggest that chronic asthma may be associated with a spectrum of GR binding defects with SR asthma at the extreme end of this range. The degree of change in GR binding affinity can be related to the magnitude of airway inflammation. This phenomenon along with the possibility of irreversible changes in the airway structure could explain refractoriness to conventional therapy. Without being bound by theory, it is believed that the significantly reduced GR binding affinity in SS asthma patients can have clinical relevance since endogenous cortisol levels regulate IgE-dependent late phase allergic reactions. Since endogenous cortisol levels are significantly lower than levels achieved after the administration of therapeutic doses of steroids, even the moderate abnormalities in GR found in SS asthmatics have an influence on the ability of endogenous glucocorticoids to suppress airway inflammation. Furthermore, even modest doses of inhaled glucocorticoids have the potential to reduce nocturnal plasma cortisol concentrations, further compromising the availability of endogenous cortisol during the critical nighttime period when pulmonary function is lowest in patients with severe asthma. Consequently, inhaled glucocorticoids can provide symptomatic relief while incompletely resolving the inflammatory process.

Since there is only one GR gene, the results of Experiment 3 suggest that Type I SR asthma, which accounts for the large majority of patients with SR asthma, is acquired and restricted to T cells, whereas Type II SR asthma is a form of primary cortisol resistance and is not limited to T cells. Reduced GR binding affinity can be induced in normal PBMC with cytokines, i.e., combination IL-2 and IL-4. SR asthma can be the end result of poorly controlled asthma and ongoing immune activation. PHA-induced T cell proliferation and cytokine production by PBMC from patients with SR asthma are poorly inhibited by the addition of dexamethasone or methylprednisolone in vitro. SR asthma can be brought under control with the combination of troleandomycin and methylprednisolone therapy, resulting in normalization of T cell sensitivity in vitro to the inhibitory effects of methylprednisolone on T lymphocyte proliferation. Furthermore, cyclosporin A, a drug whose major action is inhibition of T cell proliferation and cytokine secretion, can improve the clinical symptoms of SR asthma. Thus, without being bound by theory, it is believed that ongoing asthma inflammation and cytokine secretion may contribute to the acquired GR defect found in Type I SR asthma.

At a cellular level, glucocorticoids exert their biological effects by freely penetrating the plasma membrane and binding to a specific intracellular receptor, i.e., the GR. The unliganded receptor is thought to be a heteromer composed of a single steroid- and DNA-binding subunit and two 90-kD heat-shock proteins. The binding of glucocorticoid to its receptor results in the dissociation of the 90-kD heat-shock protein subunits and exposure of the DNA-binding site on the receptor. This activated GR complex then translocates into the nucleus and regulates transcription by binding to specific DNA sequences called glucocorticoid-responsive elements (GRE). Many of the glucocorticoid-inducible genes which have been identified are characterized by a cluster of multiple GREs upstream of their promoter and enhancer regions. The induction or repression of GR target genes ultimately results in the altered expression of glucocorticoid-regulated proteins. This latter action can be mediated via interaction of the modulatory domain of the GR with transcriptional factors, such as AP-1, NF-Kappa B, and other transcriptional regulatory elements. Overexpression of AP-1 interferes with the function of the modulatory domain of the GR. Since T cells from SR asthmatics are chronically activated and cytokines can induce elevated AP-1 levels, the latter observation provides a plausible explanation for the nuclear localization of the GR defect in SR asthma.

Primary cortisol resistance is a rare, but exists in humans and nonhuman primates. The clinical syndrome is typically familial and characterized by elevated total plasma cortisol concentrations and the absence of signs and symptoms of Cushing's syndrome. The mechanisms for end organ glucocorticoid resistance in the various reported kindreds are heterogenous and have been demonstrated to be due to reduced GR number, decreased binding affinity for glucocorticoid, or poor DNA binding of the GR to GRE. Two Type II SR asthma patients had low GR number that was not restricted to their T cells. Clinically, one of these patients presented many features consistent with primary cortisol resistance including the abilities to maintain normal plasma cortisol concentrations and to remain free of glucocorticoid adverse effects despite daily prednisone therapy in doses exceeding 20 mg/day.

Experiment 5—GR defects are a more sensitive marker of inflammation than ECP and sIL-2R.

Although there are several potential peripheral markers (i.e., cytokine levels, mediators of inflammation) which may reflect on-going inflammation, they all have limitations. First, they have not been shown to be useful in determining steroid responsiveness. Second, they only measure a specific component of the inflammatory response and thus do not provide a global assessment of the role of inflammation. Third, there are discrepancies between blood markers of inflammation and GR binding abnormalities. As an example, a patient identified as D.H. was evaluated for evidence of ongoing inflammation despite large doses of oral steroid therapy. D.H. is an individual previously documented as having steroid resistant asthma and has been shown to have a significantly diminished GR binding affinity. Examination of D.H.'s serum for markers of inflammation sIL2R and ECP revealed an ECP level in the normal range (4.3 ng/ml; geometric mean=4.4, upper limit 11.3 ng/ml), and a sIL2R level which was only slightly elevated (941 U/ml; mean 529, upper limit 913 U/ml). Nevertheless, analysis of D.H.'s bronchoalveolar lavage fluid revealed marked airway inflammation. In contrast to the ECP and sIL2R peripheral markers of inflammation or immune activation, the GR binding affinity was markedly reduced (Kd=95 nM, normal <20 nM). Thus, the altered GR binding was more sensitive in measuring ongoing immune activation and airway inflammation. This is of clinical importance because glucocorticoids were clearly not providing any therapeutic benefit and were significantly contributing to his overall morbidity, in that D.H. had several steroid-induced adverse effects including severe osteoporosis, myopathy, fragile skin, and hypertension.

Another patient, identified as M.H., displayed similar findings as patient D.H. M.H. suffered from severe poorly controlled asthma despite high dose oral steroid therapy. Evaluation of M.H.'s serum for sIL2R (537 U/ml) and ECP (9.9 ng/ml) again failed to show significant elevations in either marker. Evaluation of M.H.'s GR binding affinity revealed a significant impairment (Kd=61 nM).

Thus, analysis of GR binding parameters provided important insight into the degree of ongoing airway inflammation and into potential treatment options. Both patients were clinically unresponsive to oral steroids, and both had significant impairment in their ability to bind steroid adequately. Thus, neither patient would benefit significantly from further courses of steroids. These data also suggest that development of alternative therapies that correct the altered GR binding will reverse poor therapeutic responses to steroids in patients with severe asthma.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

What is claimed is:

1. A method for identifying animals having steroid-resistant inflammation due to a Type II nuclear glucocorticoid receptor binding abnormality, comprising:

(a) determining the nuclear glucocorticoid receptor number and nuclear glucocorticoid receptor binding affinity in nuclear glucocorticoid receptor-producing cells recovered from said animals; and (b) identifying those animals having an abnormally low number of nuclear glucocorticoid receptors and normal nuclear glucocorticoid receptor binding affinity.

2. A method for distinguishing Type I nuclear glucocorticoid receptor binding abnormalities from Type II nuclear glucocorticoid receptor binding abnormalities in an animal having Type I or Type II nuclear glucocorticoid receptor binding abnormalities comprising:

(a) determining the nuclear glucocorticoid receptor number and nuclear glucocorticoid receptor binding affinity in nuclear glucocorticoid receptor-producing T cells isolated from an animal;

(b) identifying cells with Type I nuclear glucocorticoid receptor binding abnormalities as having low nuclear glucocorticoid receptor binding affinities and high nuclear glucocorticoid receptor numbers, said Type I abnormalities being acquired; and (c) identifying cells with Type II nuclear glucocorticoid receptor binding abnormalities as having low nuclear glucocorticoid receptor numbers and normal nuclear glucocorticoid receptor binding affinities, said method useful in diagnosing steroid-resistant inflammation in an animal due to Type I or Type II glucocorticoid receptor binding abnormalities.

3. A method as claimed in claim 2, wherein the restoration of normal nuclear glucocorticoid receptor binding affinity and number in said T cells which have been cultured in vitro in the absence of IL-2 and IL-4 further identifies cells with Type I nuclear glucocorticoid receptor binding abnormalities.

4. A method as claimed in claim 2, wherein the maintenance of low nuclear glucocorticoid receptor binding affinity and high nuclear glucocorticoid receptor number in said T cells which have been cultured in vitro in the presence of IL-2 and IL-4 further identifies cells with Type I nuclear glucocorticoid receptor binding abnormalities.

5. A method as claimed in claim 1 or 2, wherein said inflammation is associated with an allergic inflammatory disorder or rheumalogical inflammatory disorder.

6. A method as claimed in claim 1 or 2, wherein said inflammation is associated with a condition selected from the group consisting of chronic allergic inflammation, asthma, atopic dermatitis, allergic rhinitis, rheumatoid arthritis and systemic lupus.

* * * * *